US011771635B2

(12) United States Patent
Ballhaus et al.

(10) Patent No.: US 11,771,635 B2
(45) Date of Patent: Oct. 3, 2023

(54) SHAMPOO COMPOSITION

(71) Applicant: The Procter & Gamble Company, Cincinnati, OH (US)

(72) Inventors: Lauren Elizabeth Ballhaus, Williamsburg, OH (US); Jean Jianqun Zhao, Cincinnati, OH (US); Nicole Marie Mazzei, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/738,713

(22) Filed: May 6, 2022

(65) Prior Publication Data
US 2022/0378680 A1    Dec. 1, 2022

Related U.S. Application Data

(60) Provisional application No. 63/276,108, filed on Nov. 5, 2021, provisional application No. 63/188,517, filed on May 14, 2021.

(51) Int. Cl.
| | | |
|---|---|---|
| A61K 8/60 | (2006.01) | |
| A61K 8/9789 | (2017.01) | |
| A61K 8/368 | (2006.01) | |
| A61K 8/49 | (2006.01) | |
| A61K 8/73 | (2006.01) | |
| A61K 8/92 | (2006.01) | |
| A61Q 5/02 | (2006.01) | |
| A61Q 17/00 | (2006.01) | |
| A61K 8/19 | (2006.01) | |

(52) U.S. Cl.
CPC .............. *A61K 8/604* (2013.01); *A61K 8/19* (2013.01); *A61K 8/368* (2013.01); *A61K 8/4926* (2013.01); *A61K 8/4946* (2013.01); *A61K 8/4953* (2013.01); *A61K 8/73* (2013.01); *A61K 8/737* (2013.01); *A61K 8/922* (2013.01); *A61K 8/9789* (2017.08); *A61Q 5/02* (2013.01); *A61Q 17/005* (2013.01); *A61K 2800/33* (2013.01); *A61K 2800/5426* (2013.01)

(58) Field of Classification Search
None
See application file for complete search history.

(56) References Cited

U.S. PATENT DOCUMENTS

| | | |
|---|---|---|
| 1,489,388 A | 4/1924 | Glenn |
| 1,600,340 A | 9/1926 | Hoffman |
| 1,612,255 A | 12/1926 | William |
| 2,438,091 A | 3/1948 | Lynch |
| 2,528,378 A | 10/1950 | Mannheimer |
| 2,658,072 A | 11/1953 | Milton |
| 2,809,971 A | 10/1957 | Jack et al. |
| 2,879,231 A | 3/1959 | Marshall |
| 3,219,656 A | 11/1965 | Boettner |
| 3,236,733 A | 2/1966 | Karsten et al. |
| 3,373,208 A | 3/1968 | Blumenthal |
| 3,636,113 A | 1/1972 | Hall |
| 3,709,437 A | 1/1973 | Wright |
| 3,716,498 A | 2/1973 | Hall |
| 3,753,196 A | 8/1973 | Kurtz et al. |
| 3,761,418 A | 9/1973 | Parran |
| 3,792,068 A | 2/1974 | Luedders et al. |
| 3,887,692 A | 6/1975 | Gilman |
| 3,904,741 A | 9/1975 | Jones et al. |
| 3,950,532 A | 4/1976 | Bouillon et al. |
| 3,959,160 A | 5/1976 | Horsler et al. |
| 4,049,792 A | 9/1977 | Elsnau |
| 4,089,945 A | 5/1978 | Brinkman et al. |
| 4,120,948 A | 10/1978 | Shelton |
| 4,137,180 A | 1/1979 | Naik |
| 4,237,155 A | 12/1980 | Kardouche |
| 4,309,119 A | 1/1982 | Wittersheim |
| 4,323,683 A | 4/1982 | Bolich, Jr. et al. |
| 4,329,334 A | 5/1982 | Su et al. |
| 4,345,080 A | 8/1982 | Bolich, Jr. |
| 4,359,456 A | 11/1982 | Gosling et al. |
| 4,379,753 A | 4/1983 | Bolich, Jr. |
| 4,430,243 A | 2/1984 | Bragg |
| 4,470,982 A | 9/1984 | Winkler |
| 4,726,945 A | 2/1988 | Patel |
| 4,732,696 A | 3/1988 | Urfer |
| 4,839,166 A | 6/1989 | Grollier et al. |
| 4,854,333 A | 8/1989 | Inman et al. |
| 4,867,971 A | 9/1989 | Ryan et al. |
| 4,931,274 A | 6/1990 | Barabino et al. |
| 4,973,416 A | 11/1990 | Kennedy |
| 4,985,238 A | 1/1991 | Tanner et al. |
| 4,997,641 A | 3/1991 | Hartnett |
| 5,019,375 A | 5/1991 | Tanner et al. |
| 5,093,112 A | 3/1992 | Birtwistle et al. |
| 5,104,646 A | 4/1992 | Bolich, Jr. |
| 5,106,609 A | 4/1992 | Bolich, Jr. |
| 5,135,747 A | 8/1992 | Faryniarz et al. |
| 5,156,834 A | 10/1992 | Beckmeyer et al. |

(Continued)

FOREIGN PATENT DOCUMENTS

| | | |
|---|---|---|
| BE | 825146 A | 8/1975 |
| BR | 199400875 A | 5/1996 |

(Continued)

OTHER PUBLICATIONS

Anonymous: "Anti-Dandruff Scalp Care Shampoo", MINTEL, Database accession No. 301924, Sep. 16, 2004, 2 pages.

(Continued)

*Primary Examiner* — Nannette Holloman
(74) *Attorney, Agent, or Firm* — John G. Powell

(57) ABSTRACT

A stable mild shampoo composition delivering consumer desired wet conditioning, moisture feel and viscosity. The shampoo may contain 5 wt % to 35 wt % of alkyl polyglucoside; 0.15 wt % to 1.05% sclerotium gum, and 0.15 wt % to 1.05% of a cationic polymer. The shampoo has a viscosity of 0.6 Pa-s to 20 Pa-s, which allows for ease of use by the consumer. It may be desirable for the shampoo to contain less than 1 wt % ionic surfactant.

13 Claims, 3 Drawing Sheets

(56) References Cited

U.S. PATENT DOCUMENTS

| | | |
|---|---|---|
| 5,294,644 A | 3/1994 | Login et al. |
| 5,296,622 A | 3/1994 | Uphues |
| 5,298,640 A | 3/1994 | Callaghan et al. |
| 5,332,569 A | 7/1994 | Wood et al. |
| 5,364,031 A | 11/1994 | Taniguchi et al. |
| 5,374,421 A | 12/1994 | Tashiro |
| 5,374,614 A | 12/1994 | Behan et al. |
| 5,409,695 A | 4/1995 | Abrutyn et al. |
| 5,415,810 A | 5/1995 | Lee et al. |
| 5,417,965 A | 5/1995 | Janchitraponvej et al. |
| 5,429,816 A | 7/1995 | Hofrichter et al. |
| 5,439,682 A | 8/1995 | Wivell |
| 5,441,659 A | 8/1995 | Minor |
| 5,486,303 A | 1/1996 | Capeci |
| 5,489,392 A | 2/1996 | Capeci |
| 5,516,448 A | 5/1996 | Capeci |
| 5,536,493 A | 7/1996 | Dubief |
| 5,554,588 A | 9/1996 | Behan et al. |
| 5,560,918 A | 10/1996 | Wivell |
| 5,565,422 A | 10/1996 | Del Greco |
| 5,569,645 A | 10/1996 | Dinniwell |
| 5,574,005 A | 11/1996 | Welch |
| 5,576,282 A | 11/1996 | Miracle |
| 5,578,298 A | 11/1996 | Berthiaume |
| 5,595,967 A | 1/1997 | Miracle |
| 5,597,936 A | 1/1997 | Perkins |
| 5,599,549 A | 2/1997 | Wivell |
| 5,624,666 A | 4/1997 | Coffindaffer et al. |
| 5,635,469 A | 6/1997 | Fowler et al. |
| 5,665,267 A | 9/1997 | Dowell et al. |
| 5,691,297 A | 11/1997 | Nassano |
| 5,714,137 A | 2/1998 | Trinh |
| 5,747,436 A | 5/1998 | Patel |
| 5,776,444 A | 7/1998 | Birtwistle et al. |
| 5,800,897 A | 9/1998 | Sharma |
| 5,816,446 A | 10/1998 | Steindorf et al. |
| 5,830,440 A | 11/1998 | Sturla et al. |
| 5,853,618 A | 12/1998 | Barker |
| 5,879,584 A | 3/1999 | Bianchetti |
| 5,891,424 A | 4/1999 | Bretzler et al. |
| 5,902,225 A | 5/1999 | Monson |
| 5,925,603 A | 7/1999 | D'Angelo |
| 5,942,217 A | 8/1999 | Woo et al. |
| 5,976,514 A | 11/1999 | Guskey et al. |
| 5,980,877 A | 11/1999 | Baravetto |
| 5,985,939 A | 11/1999 | Minor |
| 6,015,547 A | 1/2000 | Yam |
| 6,015,780 A | 1/2000 | Llosas Bigorra et al. |
| 6,020,303 A | 2/2000 | Cripe et al. |
| 6,039,933 A | 3/2000 | Samain et al. |
| 6,046,152 A | 4/2000 | Vinson et al. |
| 6,060,443 A | 5/2000 | Cripe et al. |
| 6,087,309 A | 7/2000 | Vinson et al. |
| 6,110,451 A | 8/2000 | Matz et al. |
| 6,133,222 A | 10/2000 | Vinson et al. |
| 6,139,828 A | 10/2000 | Mccullough |
| 6,153,567 A | 11/2000 | Hughes |
| 6,153,569 A | 11/2000 | Halloran |
| 6,162,834 A | 12/2000 | Sebillotte-Arnaud et al. |
| 6,180,121 B1 | 1/2001 | Guenin et al. |
| 6,225,464 B1 | 5/2001 | Hiler, II |
| 6,231,844 B1 | 5/2001 | Nambu |
| 6,232,302 B1 | 5/2001 | Alberico et al. |
| 6,248,135 B1 | 6/2001 | Trinh et al. |
| 6,268,431 B1 | 7/2001 | Snyder et al. |
| 6,284,225 B1 | 9/2001 | Bhatt |
| 6,329,331 B1 | 12/2001 | Aronson |
| 6,335,312 B1 | 1/2002 | Coffindaffer et al. |
| 6,352,688 B1 | 3/2002 | Scavone et al. |
| 6,386,392 B1 | 5/2002 | Argentieri |
| 6,413,920 B1 | 7/2002 | Bettiol |
| 6,423,305 B1 | 7/2002 | Cauwet-Martin et al. |
| 6,436,442 B1 | 8/2002 | Woo et al. |
| 6,451,300 B1 | 9/2002 | Dunlop et al. |
| 6,488,943 B1 | 12/2002 | Beerse et al. |
| 6,511,669 B1 | 1/2003 | Garnier et al. |
| 6,565,863 B1 | 5/2003 | Guillou et al. |
| 6,579,907 B1 | 6/2003 | Sebillotte-Arnaud et al. |
| 6,627,585 B1 | 9/2003 | Steer |
| 6,642,194 B2 | 11/2003 | Harrison |
| 6,649,155 B1 | 11/2003 | Dunlop et al. |
| 6,656,923 B1 | 12/2003 | Trinh |
| 6,660,288 B1 | 12/2003 | Behan et al. |
| 6,679,324 B2 | 1/2004 | Den Boer et al. |
| 6,716,455 B2 | 4/2004 | Birkel |
| 6,716,805 B1 | 4/2004 | Sherry |
| 6,740,713 B1 | 5/2004 | Busch et al. |
| 6,743,760 B1 | 6/2004 | Hardy et al. |
| 6,764,986 B1 | 7/2004 | Busch et al. |
| 6,767,507 B1 | 7/2004 | Woo et al. |
| 6,794,356 B2 | 9/2004 | Turner |
| 6,814,088 B2 | 11/2004 | Barnabas et al. |
| 6,827,795 B1 | 12/2004 | Kasturi et al. |
| 6,869,923 B1 | 3/2005 | Cunningham |
| 6,897,253 B2 | 5/2005 | Schmucker-castner |
| 6,908,889 B2 | 6/2005 | Niemiec et al. |
| 6,930,078 B2 | 8/2005 | Wells |
| 6,992,054 B2 | 1/2006 | Lee et al. |
| 7,018,978 B2 | 3/2006 | Miracle et al. |
| 7,030,068 B2 | 4/2006 | Clare et al. |
| 7,100,767 B2 | 9/2006 | Chomik et al. |
| 7,151,079 B2 | 12/2006 | Fack et al. |
| 7,172,099 B2 | 2/2007 | Hoefte |
| 7,202,198 B2 | 4/2007 | Gordon et al. |
| 7,217,752 B2 | 5/2007 | Schmucker-Castner et al. |
| 7,220,408 B2 | 5/2007 | Decoster et al. |
| 7,223,361 B2 | 5/2007 | Kvietok |
| 7,223,385 B2 | 5/2007 | Gawtrey et al. |
| 7,485,289 B2 | 2/2009 | Gawtrey et al. |
| 7,504,094 B2 | 3/2009 | Decoster et al. |
| 7,531,497 B2 | 5/2009 | Midha et al. |
| 7,541,320 B2 | 6/2009 | Dabkowski et al. |
| 7,598,213 B2 | 10/2009 | Geary et al. |
| 7,659,233 B2 | 2/2010 | Hurley et al. |
| 7,666,825 B2 | 2/2010 | Wagner et al. |
| 7,820,609 B2 | 10/2010 | Soffin et al. |
| 7,829,514 B2 | 11/2010 | Paul et al. |
| 7,841,036 B2 | 11/2010 | Smith |
| 7,867,505 B2 | 1/2011 | Elliott et al. |
| 7,928,053 B2 | 4/2011 | Hecht et al. |
| 7,977,288 B2 | 7/2011 | SenGupta |
| 8,007,545 B2 | 8/2011 | Fujii et al. |
| 8,058,500 B2 | 11/2011 | Sojka et al. |
| 8,084,407 B2 | 12/2011 | Soffin et al. |
| 8,088,721 B2 | 1/2012 | Soffin et al. |
| 8,119,168 B2 | 2/2012 | Johnson |
| 8,124,063 B2 | 2/2012 | Harichian et al. |
| 8,158,571 B2 | 4/2012 | Alonso |
| 8,300,949 B2 | 10/2012 | Xu |
| 8,322,631 B2 | 12/2012 | Richardson et al. |
| 8,343,469 B2 | 1/2013 | Bierganns et al. |
| 8,349,300 B2 | 1/2013 | Wells |
| 8,357,359 B2 | 1/2013 | Woo et al. |
| 8,361,450 B2 | 1/2013 | Johnson et al. |
| 8,388,699 B2 | 3/2013 | Wood |
| 8,401,304 B2 | 3/2013 | Cavallaro et al. |
| 8,435,501 B2 | 5/2013 | Peffly et al. |
| 8,437,556 B1 | 5/2013 | Saisan |
| 8,491,877 B2 | 7/2013 | Schwartz et al. |
| 8,539,631 B2 | 9/2013 | Catalfamo et al. |
| 8,574,561 B1 | 11/2013 | Patel et al. |
| 8,580,725 B2 | 11/2013 | Kuhlman et al. |
| 8,609,600 B2 | 12/2013 | Warr et al. |
| 8,628,760 B2 | 1/2014 | Carter et al. |
| 8,629,095 B2 | 1/2014 | Deleersnyder |
| 8,653,014 B2 | 2/2014 | Hilvert |
| 8,675,919 B2 | 3/2014 | Maladen |
| 8,679,316 B2 | 3/2014 | Brunner et al. |
| 8,680,035 B2 | 3/2014 | Kuhlman et al. |
| 8,699,751 B2 | 4/2014 | Maladen |
| 8,709,337 B2 | 4/2014 | Gruenbacher et al. |
| 8,709,385 B2 | 4/2014 | Tamarkin |
| 8,741,275 B2 | 6/2014 | Dente et al. |
| 8,741,363 B2 | 6/2014 | Albrecht et al. |

(56) References Cited

U.S. PATENT DOCUMENTS

| | | |
|---|---|---|
| 8,771,765 B1 | 7/2014 | Fernandez |
| 8,772,354 B2 | 7/2014 | Williams et al. |
| 8,795,635 B2 | 8/2014 | Tamarkin et al. |
| 8,877,316 B2 | 11/2014 | Hasenoehrl et al. |
| 8,883,698 B2 | 11/2014 | Scheibel et al. |
| 8,931,711 B2 | 1/2015 | Gruenbacher |
| 8,980,239 B2 | 3/2015 | Staudigel et al. |
| 8,987,187 B2 | 3/2015 | Smets et al. |
| 9,006,162 B1 | 4/2015 | Rizk |
| 9,186,642 B2 | 11/2015 | Dihora et al. |
| 9,187,407 B2 | 11/2015 | Koshti et al. |
| 9,265,727 B1 | 2/2016 | Lowenborg |
| 9,272,164 B2 | 3/2016 | Johnson et al. |
| 9,296,550 B2 | 3/2016 | Smith |
| 9,308,398 B2 | 4/2016 | Hutton et al. |
| 9,393,447 B2 | 7/2016 | Zasloff |
| 9,428,616 B2 | 8/2016 | Wagner |
| 9,512,275 B2 | 12/2016 | Wagner |
| 9,610,239 B2 | 4/2017 | Feng |
| 9,655,821 B2 | 5/2017 | Carter et al. |
| 9,662,291 B2 | 5/2017 | Johnson et al. |
| 9,682,021 B2 | 6/2017 | Tamarkin et al. |
| 9,776,787 B2 | 10/2017 | Nakajima |
| 9,949,901 B2 | 4/2018 | Zhao et al. |
| 9,949,911 B2 | 4/2018 | Cetti |
| 9,968,535 B2 | 5/2018 | Kitko |
| 9,968,537 B2 | 5/2018 | Sharma |
| 9,993,419 B2 | 6/2018 | Glenn, Jr. |
| 9,993,420 B2 | 6/2018 | Glenn, Jr. et al. |
| 10,039,706 B2 | 8/2018 | Meralli et al. |
| 10,039,939 B2 | 8/2018 | Xavier et al. |
| 10,113,140 B2 | 10/2018 | Frankenbach |
| 10,182,976 B2 | 1/2019 | Staudigel |
| 10,238,685 B2 | 3/2019 | Dunn et al. |
| 10,265,261 B2 | 4/2019 | Park et al. |
| 10,311,575 B2 | 6/2019 | Stofel |
| 10,392,625 B2 | 8/2019 | Jin et al. |
| 10,426,713 B2 | 10/2019 | Song |
| 10,441,519 B2 | 10/2019 | Zhao |
| 10,552,557 B2 | 2/2020 | Frankenbach et al. |
| 10,610,473 B2 | 4/2020 | Hertenstein et al. |
| 10,653,590 B2 | 5/2020 | Torres Rivera |
| 10,799,434 B2 | 10/2020 | Torres Rivera |
| 10,842,720 B2 | 11/2020 | Thompson |
| 10,881,597 B2 | 1/2021 | Lane et al. |
| 10,888,505 B2 | 1/2021 | Johnson |
| 10,912,732 B2 | 2/2021 | Gillis |
| 11,116,703 B2 | 9/2021 | Song et al. |
| 11,116,704 B2 | 9/2021 | Song et al. |
| 11,129,775 B2 | 9/2021 | Song et al. |
| 11,334,694 B2 | 5/2022 | Cetti et al. |
| 11,334,695 B2 | 5/2022 | Cetti et al. |
| 2001/0000467 A1 | 4/2001 | Murray |
| 2001/0006088 A1 | 7/2001 | Lyle |
| 2001/0006621 A1 | 7/2001 | Coupe et al. |
| 2001/0016565 A1 | 8/2001 | Bodet et al. |
| 2002/0012646 A1 | 1/2002 | Royce et al. |
| 2002/0028182 A1 | 3/2002 | Dawson |
| 2002/0037299 A1 | 3/2002 | Turowski-Wanke et al. |
| 2002/0172648 A1 | 11/2002 | Hehner et al. |
| 2002/0193265 A1 | 12/2002 | Perron et al. |
| 2002/0197213 A1 | 12/2002 | Schmenger et al. |
| 2003/0003070 A1 | 1/2003 | Eggers et al. |
| 2003/0008787 A1 | 1/2003 | Mcgee et al. |
| 2003/0022799 A1 | 1/2003 | Alvarado et al. |
| 2003/0049292 A1 | 3/2003 | Turowski-Wanke et al. |
| 2003/0050150 A1 | 3/2003 | Tanaka |
| 2003/0059377 A1 | 3/2003 | Riley |
| 2003/0083210 A1 | 5/2003 | Goldberg |
| 2003/0108501 A1 | 6/2003 | Hofrichter |
| 2003/0147842 A1 | 8/2003 | Restle et al. |
| 2003/0154561 A1 | 8/2003 | Patel |
| 2003/0161802 A1 | 8/2003 | Flammer |
| 2003/0180238 A1 | 9/2003 | Sakurai et al. |
| 2003/0180246 A1 | 9/2003 | Frantz et al. |
| 2003/0185867 A1 | 10/2003 | Kerschner et al. |
| 2003/0192922 A1 | 10/2003 | Ceppaluni et al. |
| 2003/0202952 A1 | 10/2003 | Wells et al. |
| 2003/0223951 A1 | 12/2003 | Geary et al. |
| 2003/0228272 A1 | 12/2003 | Amjad et al. |
| 2004/0014879 A1 | 1/2004 | Denzer et al. |
| 2004/0064117 A1 | 4/2004 | Hammons |
| 2004/0144863 A1 | 7/2004 | Kendrick |
| 2004/0151793 A1 | 8/2004 | Paspaleeva-kuhn et al. |
| 2004/0157754 A1 | 8/2004 | Geary et al. |
| 2004/0229963 A1 | 11/2004 | Stephane |
| 2004/0234484 A1 | 11/2004 | Peffly |
| 2004/0235689 A1 | 11/2004 | Sakai et al. |
| 2005/0003975 A1 | 1/2005 | Browne et al. |
| 2005/0003980 A1 | 1/2005 | Baker |
| 2005/0020468 A1 | 1/2005 | Frantz et al. |
| 2005/0136011 A1 | 6/2005 | Nekludoff |
| 2005/0152863 A1 | 7/2005 | Brautigam |
| 2005/0192207 A1 | 9/2005 | Morgan, III et al. |
| 2005/0201967 A1 | 9/2005 | Albrecht et al. |
| 2005/0202984 A1 | 9/2005 | Schwartz et al. |
| 2005/0227902 A1 | 10/2005 | Erazo-majewicz et al. |
| 2005/0233929 A1 | 10/2005 | Queen |
| 2005/0245407 A1 | 11/2005 | Ishihara |
| 2005/0276831 A1 | 12/2005 | Dihora |
| 2006/0002880 A1 | 1/2006 | Peffly |
| 2006/0005333 A1 | 1/2006 | Catalfamo et al. |
| 2006/0009337 A1 | 1/2006 | Smith |
| 2006/0030509 A1 | 2/2006 | Modi |
| 2006/0034778 A1 | 2/2006 | Kitano et al. |
| 2006/0057075 A1 | 3/2006 | Arkin et al. |
| 2006/0057097 A1 | 3/2006 | Derici |
| 2006/0079417 A1 | 4/2006 | Wagner |
| 2006/0079418 A1 | 4/2006 | Wagner et al. |
| 2006/0079419 A1 | 4/2006 | Wagner et al. |
| 2006/0079420 A1 | 4/2006 | Wagner et al. |
| 2006/0079421 A1 | 4/2006 | Wagner et al. |
| 2006/0084589 A1 | 4/2006 | Vlad et al. |
| 2006/0090777 A1 | 5/2006 | Hecht et al. |
| 2006/0094610 A1 | 5/2006 | Yamato et al. |
| 2006/0110415 A1 | 5/2006 | Gupta |
| 2006/0120982 A1 | 6/2006 | Derici et al. |
| 2006/0120988 A1 | 6/2006 | Bailey et al. |
| 2006/0135397 A1 | 6/2006 | Bissey-beugras |
| 2006/0166857 A1 | 7/2006 | Surburg et al. |
| 2006/0171911 A1 | 8/2006 | Schwartz et al. |
| 2006/0183662 A1 | 8/2006 | Crotty |
| 2006/0210139 A1 | 9/2006 | Carroll |
| 2006/0229227 A1 | 10/2006 | Goldman |
| 2006/0252662 A1 | 11/2006 | Soffin |
| 2006/0263319 A1 | 11/2006 | Fan et al. |
| 2006/0276357 A1 | 12/2006 | Smith, III et al. |
| 2006/0292104 A1 | 12/2006 | Guskey |
| 2007/0003499 A1 | 1/2007 | Shen et al. |
| 2007/0020263 A1 | 1/2007 | Shitara et al. |
| 2007/0072781 A1 | 3/2007 | Soffin et al. |
| 2007/0110700 A1 | 5/2007 | Wells |
| 2007/0154402 A1 | 7/2007 | Trumbore et al. |
| 2007/0155637 A1 | 7/2007 | Smith et al. |
| 2007/0160555 A1 | 7/2007 | Staudigel |
| 2007/0179207 A1 | 8/2007 | Fernandez de Castro et al. |
| 2007/0225193 A1 | 9/2007 | Kuhlman et al. |
| 2007/0269397 A1 | 11/2007 | Terada |
| 2007/0275866 A1 | 11/2007 | Dykstra |
| 2007/0292380 A1 | 12/2007 | Staudigel |
| 2007/0298994 A1 | 12/2007 | Finke et al. |
| 2008/0003245 A1 | 1/2008 | Kroepke et al. |
| 2008/0008668 A1 | 1/2008 | Harichian et al. |
| 2008/0019928 A1 | 1/2008 | Franzke |
| 2008/0063618 A1 | 3/2008 | Johnson |
| 2008/0138442 A1 | 6/2008 | Johnson |
| 2008/0152610 A1 | 6/2008 | Cajan |
| 2008/0160093 A1 | 7/2008 | Schwartz et al. |
| 2008/0176780 A1 | 7/2008 | Warr |
| 2008/0194454 A1 | 8/2008 | Morgan |
| 2008/0206179 A1 | 8/2008 | Peffly et al. |
| 2008/0260655 A1 | 10/2008 | Tamarkin et al. |
| 2008/0260665 A1 | 10/2008 | Guerchet et al. |
| 2008/0261844 A1 | 10/2008 | Ruppert et al. |

(56) References Cited

U.S. PATENT DOCUMENTS

| | | |
|---|---|---|
| 2008/0317698 A1 | 12/2008 | Wells et al. |
| 2009/0005280 A1 | 1/2009 | Woo et al. |
| 2009/0029900 A1 | 1/2009 | Cetti et al. |
| 2009/0041702 A1 | 2/2009 | Molenda |
| 2009/0062406 A1 | 3/2009 | Loeffler |
| 2009/0155383 A1 | 6/2009 | Kitko et al. |
| 2009/0178210 A1 | 7/2009 | Bistram |
| 2009/0197784 A1 | 8/2009 | Ainger |
| 2009/0221463 A1 | 9/2009 | Kitko et al. |
| 2009/0240223 A1 | 9/2009 | Warren |
| 2009/0246236 A1 | 10/2009 | Kitko |
| 2009/0312223 A1 | 12/2009 | Yang et al. |
| 2009/0312224 A1 | 12/2009 | Yang et al. |
| 2009/0324505 A1 | 12/2009 | Seidling |
| 2010/0000116 A1 | 1/2010 | Aouad et al. |
| 2010/0001116 A1 | 1/2010 | Johnson |
| 2010/0009285 A1 | 1/2010 | Daems et al. |
| 2010/0061946 A1 | 3/2010 | Scherner et al. |
| 2010/0087357 A1 | 4/2010 | Morgan, III et al. |
| 2010/0152083 A1 | 6/2010 | Velazquez |
| 2010/0168251 A1 | 7/2010 | Warr et al. |
| 2010/0183539 A1 | 7/2010 | Bernhardt |
| 2010/0215775 A1 | 8/2010 | Schmaus et al. |
| 2010/0287710 A1 | 11/2010 | Denutte et al. |
| 2010/0310644 A1 | 12/2010 | Liebmann |
| 2010/0322878 A1 | 12/2010 | Stella et al. |
| 2011/0008267 A1 | 1/2011 | Arkin et al. |
| 2011/0023266 A1 | 2/2011 | Gross et al. |
| 2011/0098209 A1 | 4/2011 | Smets et al. |
| 2011/0107524 A1 | 5/2011 | Chieffi et al. |
| 2011/0118691 A1 | 5/2011 | Nishitani |
| 2011/0139170 A1 | 6/2011 | Hippe et al. |
| 2011/0150815 A1 | 6/2011 | Woo et al. |
| 2011/0165107 A1 | 7/2011 | Derks et al. |
| 2011/0171155 A1 | 7/2011 | Federle |
| 2011/0177017 A1 | 7/2011 | Coffindaffer et al. |
| 2011/0232668 A1 | 9/2011 | Hoffmann et al. |
| 2011/0245126 A1 | 10/2011 | Tsaur et al. |
| 2011/0245134 A1 | 10/2011 | Smets |
| 2011/0245136 A1 | 10/2011 | Smets |
| 2011/0268778 A1 | 11/2011 | Dihora et al. |
| 2011/0269657 A1 | 11/2011 | Dihora |
| 2011/0300095 A1 | 12/2011 | Dente et al. |
| 2011/0303766 A1 | 12/2011 | Smith |
| 2011/0305739 A1 | 12/2011 | Royce |
| 2011/0305778 A1 | 12/2011 | Caggioni et al. |
| 2011/0308555 A1 | 12/2011 | Smets et al. |
| 2011/0308556 A1 | 12/2011 | Smets et al. |
| 2011/0319790 A1 | 12/2011 | Kost et al. |
| 2012/0004328 A1 | 1/2012 | Huchel et al. |
| 2012/0009285 A1 | 1/2012 | Wei et al. |
| 2012/0014901 A1 | 1/2012 | Sunkel et al. |
| 2012/0031419 A1 | 2/2012 | Batt |
| 2012/0034173 A1 | 2/2012 | Batt |
| 2012/0052031 A1 | 3/2012 | Troccaz et al. |
| 2012/0100091 A1 | 4/2012 | Hata et al. |
| 2012/0100092 A1 | 4/2012 | Murray |
| 2012/0129924 A1 | 5/2012 | Park et al. |
| 2012/0219610 A1 | 8/2012 | Smith, III et al. |
| 2012/0230936 A1 | 9/2012 | Mikkelsen |
| 2012/0237469 A1 | 9/2012 | Dente et al. |
| 2012/0246851 A1 | 10/2012 | Smith, III et al. |
| 2012/0258150 A1 | 10/2012 | Rauckhorst et al. |
| 2012/0291911 A1 | 11/2012 | Smith |
| 2012/0309660 A1 | 12/2012 | Kawasoe |
| 2012/0316095 A1 | 12/2012 | Wei et al. |
| 2013/0029932 A1 | 1/2013 | Kachi et al. |
| 2013/0034515 A1 | 2/2013 | Stone et al. |
| 2013/0043145 A1 | 2/2013 | Smith, III et al. |
| 2013/0043146 A1 | 2/2013 | Smith, III et al. |
| 2013/0043147 A1 | 2/2013 | Smith, III et al. |
| 2013/0045285 A1 | 2/2013 | Stella et al. |
| 2013/0053295 A1 | 2/2013 | Kinoshita et al. |
| 2013/0053300 A1 | 2/2013 | Scheibel et al. |
| 2013/0089587 A1 | 4/2013 | Staudigel |
| 2013/0115173 A1 | 5/2013 | Trumbore et al. |
| 2013/0143784 A1 | 6/2013 | Rizk |
| 2013/0150338 A1 | 6/2013 | Ananthapadmanabhan |
| 2013/0156712 A1 | 6/2013 | Frantz |
| 2013/0189212 A1 | 7/2013 | Jawale et al. |
| 2013/0211952 A1 | 8/2013 | Sugaya |
| 2013/0216491 A1 | 8/2013 | Ogihara et al. |
| 2013/0243718 A1 | 9/2013 | Pasquet |
| 2013/0244922 A1 | 9/2013 | Bartelt |
| 2013/0266642 A1 | 10/2013 | Hollingshead et al. |
| 2013/0280192 A1 | 10/2013 | Carter et al. |
| 2013/0280202 A1 | 10/2013 | Stella et al. |
| 2013/0284195 A1 | 10/2013 | Murdock |
| 2013/0296289 A1 | 11/2013 | Hall et al. |
| 2013/0319463 A1 | 12/2013 | Policicchio |
| 2014/0037703 A1 | 2/2014 | Dihora et al. |
| 2014/0039066 A1 | 2/2014 | Grimadell et al. |
| 2014/0086893 A1 | 3/2014 | Gutmann et al. |
| 2014/0112879 A1 | 4/2014 | Molenda et al. |
| 2014/0127149 A1 | 5/2014 | Lepilleur |
| 2014/0131395 A1 | 5/2014 | Chang |
| 2014/0134125 A1 | 5/2014 | Dahl |
| 2014/0162979 A1 | 6/2014 | Palla-venkata |
| 2014/0171471 A1 | 6/2014 | Krueger |
| 2014/0186864 A1 | 7/2014 | Kato et al. |
| 2014/0201927 A1 | 7/2014 | Bianchetti et al. |
| 2014/0216495 A1 | 8/2014 | Bureiko |
| 2014/0221269 A1 | 8/2014 | Sobel et al. |
| 2014/0228268 A1 | 8/2014 | Fahl et al. |
| 2014/0237732 A1 | 8/2014 | Zuedel Fernandes et al. |
| 2014/0246515 A1 | 9/2014 | Nakajima |
| 2014/0308227 A1 | 10/2014 | Mabille |
| 2014/0309154 A1 | 10/2014 | Carter et al. |
| 2014/0335041 A1 | 11/2014 | Peffly et al. |
| 2014/0348884 A1 | 11/2014 | Hilvert et al. |
| 2014/0348886 A1 | 11/2014 | Johnson et al. |
| 2014/0349902 A1 | 11/2014 | Allef et al. |
| 2015/0017152 A1 | 1/2015 | Potechin et al. |
| 2015/0021496 A1 | 1/2015 | Shabbir |
| 2015/0037273 A1 | 2/2015 | Wagner |
| 2015/0050231 A1 | 2/2015 | Murase |
| 2015/0071977 A1 | 3/2015 | Dihora |
| 2015/0093420 A1 | 4/2015 | Snyder |
| 2015/0093429 A1 | 4/2015 | Carter et al. |
| 2015/0098921 A1 | 4/2015 | Franzke et al. |
| 2015/0099684 A1 | 4/2015 | Boutique |
| 2015/0108163 A1 | 4/2015 | Smith et al. |
| 2015/0110728 A1 | 4/2015 | Jayaswal |
| 2015/0141310 A1 | 5/2015 | Smets et al. |
| 2015/0147286 A1 | 5/2015 | Barrera |
| 2015/0157548 A1 | 6/2015 | De Feij et al. |
| 2015/0218496 A1 | 8/2015 | Schmiedel et al. |
| 2015/0231045 A1 | 8/2015 | Krohn et al. |
| 2015/0262354 A1 | 9/2015 | Periaswamy |
| 2015/0297489 A1 | 10/2015 | Kleinen et al. |
| 2015/0299400 A1 | 10/2015 | Wagner et al. |
| 2015/0313818 A1 | 11/2015 | Stagg |
| 2015/0352027 A1 | 12/2015 | Thomas et al. |
| 2015/0359725 A1 | 12/2015 | Glenn, Jr. et al. |
| 2015/0359726 A1 | 12/2015 | Glenn, Jr. et al. |
| 2015/0359728 A1 | 12/2015 | Glenn, Jr. et al. |
| 2016/0008257 A1 | 1/2016 | Zhou et al. |
| 2016/0022566 A1 | 1/2016 | Figura |
| 2016/0089317 A1 | 3/2016 | Cetti et al. |
| 2016/0089318 A1 | 3/2016 | Cetti et al. |
| 2016/0089322 A1 | 3/2016 | Santos Nogueira et al. |
| 2016/0089462 A1 | 3/2016 | Frankenbach |
| 2016/0089464 A1 | 3/2016 | Frankenbach et al. |
| 2016/0089465 A1 | 3/2016 | Frankenbach et al. |
| 2016/0090555 A1 | 3/2016 | Frankenbach |
| 2016/0090556 A1 | 3/2016 | Frankenbach et al. |
| 2016/0090557 A1 | 3/2016 | Frankenbach et al. |
| 2016/0090558 A1 | 3/2016 | Frankenbach et al. |
| 2016/0092661 A1 | 3/2016 | Hollingshead et al. |
| 2016/0095804 A1 | 4/2016 | Xavier et al. |
| 2016/0113849 A1 | 4/2016 | Grimadell et al. |
| 2016/0128944 A1 | 5/2016 | Chawrai |
| 2016/0193125 A1 | 7/2016 | Jones et al. |
| 2016/0206522 A1 | 7/2016 | Ribaut et al. |

(56) References Cited

U.S. PATENT DOCUMENTS

| | | |
|---|---|---|
| 2016/0235643 A1 | 8/2016 | Mathonneau et al. |
| 2016/0250115 A1 | 9/2016 | Li et al. |
| 2016/0279048 A1 | 9/2016 | Jayaswal et al. |
| 2016/0287503 A1 | 10/2016 | Schroeder |
| 2016/0287509 A1 | 10/2016 | Peffly |
| 2016/0296656 A1 | 10/2016 | Scavone et al. |
| 2016/0303043 A1 | 10/2016 | Khoury |
| 2016/0306909 A1 | 10/2016 | Hollingshead et al. |
| 2016/0309871 A1 | 10/2016 | Torres Rivera et al. |
| 2016/0310369 A1 | 10/2016 | Thompson et al. |
| 2016/0310370 A1 | 10/2016 | Zhao et al. |
| 2016/0310371 A1 | 10/2016 | Zhao |
| 2016/0310375 A1 | 10/2016 | Torres Rivera |
| 2016/0310386 A1 | 10/2016 | Smith, III et al. |
| 2016/0310388 A1 | 10/2016 | Smith, III et al. |
| 2016/0310389 A1 | 10/2016 | Thompson et al. |
| 2016/0310390 A1 | 10/2016 | Smith, III et al. |
| 2016/0310391 A1 | 10/2016 | Smith, III et al. |
| 2016/0310393 A1 | 10/2016 | Chang et al. |
| 2016/0310402 A1 | 10/2016 | Zhao et al. |
| 2016/0317424 A1 | 11/2016 | Kadir et al. |
| 2016/0326458 A1 | 11/2016 | Smets et al. |
| 2016/0354300 A1 | 12/2016 | Thompson et al. |
| 2017/0066579 A1 | 3/2017 | Zillges |
| 2017/0071837 A1 | 3/2017 | Schelges et al. |
| 2017/0101609 A1 | 4/2017 | Vargas |
| 2017/0110690 A1 | 4/2017 | Lamansky et al. |
| 2017/0110695 A1 | 4/2017 | Nishikawa et al. |
| 2017/0119917 A1 | 5/2017 | Frankenbach et al. |
| 2017/0137752 A1 | 5/2017 | Frankenbach et al. |
| 2017/0137753 A1 | 5/2017 | Frankenbach et al. |
| 2017/0165164 A1 | 6/2017 | Zhao et al. |
| 2017/0165165 A1 | 6/2017 | Zhao et al. |
| 2017/0209359 A1 | 7/2017 | Zhao et al. |
| 2017/0239155 A1 | 8/2017 | Hartnett |
| 2017/0249407 A1 | 8/2017 | Cetti et al. |
| 2017/0249408 A1 | 8/2017 | Cetti et al. |
| 2017/0252273 A1 | 9/2017 | Renock et al. |
| 2017/0255725 A1 | 9/2017 | Frankenbach et al. |
| 2017/0278249 A1 | 9/2017 | Stofel |
| 2017/0283959 A1 | 10/2017 | Shellef |
| 2017/0304172 A1 | 10/2017 | Chang et al. |
| 2017/0304184 A1 | 10/2017 | Glenn, Jr. |
| 2017/0304185 A1 | 10/2017 | Glenn, Jr. et al. |
| 2017/0304186 A1 | 10/2017 | Glenn, Jr. |
| 2017/0333321 A1 | 11/2017 | Carnali |
| 2017/0333591 A9 | 11/2017 | Scavone et al. |
| 2017/0367963 A1 | 12/2017 | Kadir et al. |
| 2018/0004875 A1 | 1/2018 | Cetti et al. |
| 2018/0044097 A1 | 2/2018 | Zeik |
| 2018/0057451 A1 | 3/2018 | Owens et al. |
| 2018/0066210 A1 | 3/2018 | Frankenbach et al. |
| 2018/0110594 A1 | 4/2018 | Atkin |
| 2018/0110688 A1 | 4/2018 | Torres Rivera et al. |
| 2018/0110689 A1 | 4/2018 | Torres Rivera et al. |
| 2018/0110690 A1 | 4/2018 | Torres Rivera |
| 2018/0110691 A1 | 4/2018 | Torres Rivera et al. |
| 2018/0110692 A1 | 4/2018 | Torres Rivera et al. |
| 2018/0110693 A1 | 4/2018 | Renock et al. |
| 2018/0110694 A1 | 4/2018 | Renock et al. |
| 2018/0110695 A1 | 4/2018 | Thompson |
| 2018/0110696 A1 | 4/2018 | Johnson et al. |
| 2018/0110704 A1 | 4/2018 | Zhao et al. |
| 2018/0110707 A1 | 4/2018 | Zhao et al. |
| 2018/0110710 A1 | 4/2018 | Zhao et al. |
| 2018/0110714 A1 | 4/2018 | Glenn, Jr. et al. |
| 2018/0116937 A1 | 5/2018 | Park et al. |
| 2018/0116941 A1 | 5/2018 | Wang |
| 2018/0133133 A1 | 5/2018 | Kleinen et al. |
| 2018/0177708 A1 | 6/2018 | Lee et al. |
| 2018/0221266 A1 | 8/2018 | Zhao et al. |
| 2018/0256481 A1 | 9/2018 | Glenn, Jr. |
| 2018/0280270 A1 | 10/2018 | Rughani et al. |
| 2018/0311135 A1 | 11/2018 | Chang |
| 2018/0311136 A1 | 11/2018 | Chang |
| 2018/0318194 A1 | 11/2018 | Hoffmann et al. |
| 2018/0344611 A1 | 12/2018 | Zhao et al. |
| 2018/0344612 A1 | 12/2018 | Zhao et al. |
| 2018/0344613 A1 | 12/2018 | Zhao et al. |
| 2018/0344614 A1 | 12/2018 | Zhao et al. |
| 2018/0360713 A1 | 12/2018 | Jouy et al. |
| 2019/0105242 A1 | 4/2019 | Song |
| 2019/0105243 A1 | 4/2019 | Song |
| 2019/0105244 A1 | 4/2019 | Song |
| 2019/0105245 A1 | 4/2019 | Song |
| 2019/0105246 A1 | 4/2019 | Cochran |
| 2019/0105247 A1 | 4/2019 | Song |
| 2019/0117543 A1 | 4/2019 | Zhao |
| 2019/0117544 A1 | 4/2019 | Zhao |
| 2019/0117545 A1 | 4/2019 | Zhao |
| 2019/0125650 A1 | 5/2019 | Lee et al. |
| 2019/0142711 A1 | 5/2019 | Torres Rivera |
| 2019/0142800 A1 | 5/2019 | Ghosh et al. |
| 2019/0155975 A9 | 5/2019 | Cetti et al. |
| 2019/0167554 A1 | 6/2019 | Wankhade |
| 2019/0183777 A1 | 6/2019 | Gillis |
| 2019/0183778 A1 | 6/2019 | Glenn, Jr. |
| 2019/0192405 A1 | 6/2019 | Zhao |
| 2019/0240121 A1 | 8/2019 | Torres Rivera |
| 2019/0307298 A1 | 10/2019 | Zhao |
| 2019/0328647 A1 | 10/2019 | Chang et al. |
| 2019/0365619 A1* | 12/2019 | Ceballos ............... A61K 8/466 |
| 2019/0365633 A1 | 12/2019 | Glenn, Jr. |
| 2020/0000690 A1 | 1/2020 | Renock |
| 2020/0078284 A1 | 3/2020 | Botto et al. |
| 2020/0129402 A1 | 4/2020 | Jamadagni |
| 2020/0163846 A1 | 5/2020 | Song |
| 2020/0170894 A1 | 6/2020 | Park et al. |
| 2020/0197272 A1 | 6/2020 | Hertenstein et al. |
| 2020/0206110 A1 | 7/2020 | Hertenstein et al. |
| 2020/0237628 A1 | 7/2020 | Torres Rivera |
| 2021/0022986 A1 | 1/2021 | Glenn, Jr. |
| 2021/0093543 A1 | 4/2021 | Parikh et al. |
| 2021/0121385 A1 | 4/2021 | Muller et al. |
| 2021/0128444 A1 | 5/2021 | Muller et al. |
| 2021/0128447 A1 | 5/2021 | Galpin et al. |
| 2021/0169765 A1 | 6/2021 | Renock |
| 2021/0212927 A1 | 7/2021 | Hutton, III et al. |
| 2021/0267853 A1 | 9/2021 | Johnson et al. |
| 2021/0275410 A1 | 9/2021 | Hutton, III |
| 2021/0353518 A1 | 11/2021 | Ballhaus et al. |
| 2021/0353522 A1 | 11/2021 | Ballhaus et al. |
| 2021/0401716 A1* | 12/2021 | Gogineni ............... A61K 8/604 |
| 2022/0062136 A1 | 3/2022 | Feng |
| 2022/0160606 A1 | 5/2022 | Renock |
| 2022/0175640 A1 | 6/2022 | Herteinstein et al. |
| 2022/0378684 A1 | 12/2022 | Cochran et al. |
| 2022/0395444 A1 | 12/2022 | Hutton, III |
| 2023/0053056 A1 | 2/2023 | Renock et al. |

FOREIGN PATENT DOCUMENTS

| | | |
|---|---|---|
| CA | 704195 A | 2/1965 |
| CA | 1248458 A | 1/1989 |
| CA | 2078375 A1 | 3/1994 |
| CN | 1263455 A | 8/2000 |
| CN | 1286612 A | 3/2001 |
| CN | 1545404 A | 11/2004 |
| CN | 1823929 A | 8/2006 |
| CN | 100534415 C | 9/2009 |
| CN | 101112349 B | 5/2011 |
| CN | 101690697 B | 10/2011 |
| CN | 101559034 B | 1/2013 |
| CN | 102895151 A | 1/2013 |
| CN | 102973437 A | 3/2013 |
| CN | 102697668 B | 8/2013 |
| CN | 103356408 A | 10/2013 |
| CN | 102697670 B | 7/2014 |
| CN | 104107401 A | 10/2014 |
| CN | 102851015 B | 12/2014 |
| CN | 105726393 A | 7/2016 |
| CN | 105769617 A | 7/2016 |
| CN | 106659664 A | 5/2017 |
| CN | 106750361 A | 5/2017 |

(56) References Cited

FOREIGN PATENT DOCUMENTS

| | | |
|---|---|---|
| CN | 107595657 A | 1/2018 |
| CN | 107595673 A | 1/2018 |
| CN | 107648096 A | 2/2018 |
| CN | 107737329 A | 2/2018 |
| CN | 108186385 A | 6/2018 |
| CN | 108283583 A | 7/2018 |
| CN | 110279591 A | 9/2019 |
| DE | 2145204 A1 | 3/1973 |
| DE | 3018456 A1 | 11/1981 |
| DE | 4315396 A1 | 11/1994 |
| DE | 102004012009 A1 | 9/2005 |
| DE | 202005009618 U1 | 9/2005 |
| DE | 102004023720 A1 | 12/2005 |
| DE | 102014225083 A1 | 10/2015 |
| DE | 102014225606 A1 | 10/2015 |
| DE | 102015204987 A1 | 9/2016 |
| EP | 0108517 A2 | 5/1984 |
| EP | 0574086 A2 | 12/1993 |
| EP | 0666358 A1 | 8/1995 |
| EP | 0674898 A2 | 10/1995 |
| EP | 1340485 A2 | 2/2003 |
| EP | 1346720 A2 | 9/2003 |
| EP | 067898 B2 | 3/2006 |
| EP | 1714678 A1 | 10/2006 |
| EP | 1842572 A2 | 10/2007 |
| EP | 2005939 A1 | 12/2008 |
| EP | 1970045 A3 | 9/2009 |
| EP | 2042216 B1 | 9/2015 |
| EP | 3260171 A1 | 12/2017 |
| EP | 3622946 A1 | 3/2020 |
| ES | 2052450 B1 | 12/1994 |
| FR | 2669531 A1 | 5/1992 |
| FR | 2795955 A1 | 1/2001 |
| GB | 190110699 A | 8/1901 |
| GB | 191023922 A | 10/1911 |
| GB | 1347950 A | 2/1974 |
| GB | 2048229 | 12/1980 |
| GB | 2450727 A | 1/2009 |
| HU | 42318 | 8/1986 |
| JP | S56011009 A | 12/1981 |
| JP | S58113300 A | 7/1983 |
| JP | S58198412 A | 11/1983 |
| JP | AS60004598 A | 1/1985 |
| JP | S61236708 A | 10/1986 |
| JP | S62205200 A | 9/1987 |
| JP | S63165308 A | 7/1988 |
| JP | H04364114 A | 12/1992 |
| JP | H06220495 A | 8/1994 |
| JP | 07252134 A | 10/1995 |
| JP | H08310924 A | 11/1996 |
| JP | 09020618 A | 1/1997 |
| JP | 09030938 A | 2/1997 |
| JP | H09175961 A | 7/1997 |
| JP | H10017894 A | 1/1998 |
| JP | 2964226 B2 | 10/1999 |
| JP | 2000178586 A | 6/2000 |
| JP | 3069802 B2 | 7/2000 |
| JP | 2001011492 A | 1/2001 |
| JP | 2001011497 A | 1/2001 |
| JP | 2001254099 A | 9/2001 |
| JP | 2001261529 A | 9/2001 |
| JP | 2003201217 A | 12/2001 |
| JP | 2002179552 A | 6/2002 |
| JP | 2002226889 A | 8/2002 |
| JP | 2002336337 A | 11/2002 |
| JP | 2003055699 A | 2/2003 |
| JP | 2003082398 A | 3/2003 |
| JP | 2003171688 A | 6/2003 |
| JP | 2003176497 A | 6/2003 |
| JP | 2003261413 A | 9/2003 |
| JP | 2003268398 A | 9/2003 |
| JP | 3480165 B2 | 12/2003 |
| JP | 2003342131 A | 12/2003 |
| JP | 3634988 B2 | 3/2005 |
| JP | 3634991 B2 | 3/2005 |
| JP | 3634996 B2 | 3/2005 |
| JP | 2005187359 A | 7/2005 |
| JP | 2005232113 A | 9/2005 |
| JP | 2006063044 A | 3/2006 |
| JP | 2006104149 A | 4/2006 |
| JP | 2006124312 A | 5/2006 |
| JP | 2006183039 A | 7/2006 |
| JP | 2006193549 A | 7/2006 |
| JP | 2006249092 A | 9/2006 |
| JP | 2006282565 A | 10/2006 |
| JP | 2007131687 A | 5/2007 |
| JP | 2007177047 A | 7/2007 |
| JP | 2007223935 A | 9/2007 |
| JP | 2008001626 A | 1/2008 |
| JP | 2008214292 A | 9/2008 |
| JP | 2009096778 A | 5/2009 |
| JP | 2009120559 A | 6/2009 |
| JP | 2009161866 A | 7/2009 |
| JP | 2011153167 A | 8/2011 |
| JP | 2011190221 A | 9/2011 |
| JP | 2011241353 A | 12/2011 |
| JP | 5041113 B2 | 7/2012 |
| JP | 2013010757 A | 1/2013 |
| JP | 2013091641 A | 5/2013 |
| JP | 2013151434 A | 8/2013 |
| JP | 2013155143 A | 8/2013 |
| JP | 2013216639 A | 10/2013 |
| JP | 6046394 B2 | 1/2014 |
| JP | 2014024875 A | 2/2014 |
| JP | 2014091723 A | 5/2014 |
| JP | 2014234350 A | 12/2014 |
| JP | 5667790 B2 | 2/2015 |
| JP | 2015101545 A | 6/2015 |
| JP | 2016013973 A | 1/2016 |
| JP | 2016088910 A | 5/2016 |
| JP | 6184550 B1 | 8/2017 |
| JP | 2018012673 A | 1/2018 |
| KR | 100290589 B1 | 9/2001 |
| KR | 100821846 B1 | 4/2008 |
| KR | 1020080111280 A | 12/2008 |
| KR | 20090095359 A | 9/2009 |
| KR | 20100040180 A | 4/2010 |
| KR | 20140060882 A | 5/2014 |
| KR | 101494008 B1 | 2/2015 |
| KR | 101503922 B1 | 3/2015 |
| KR | 101532070 B1 | 7/2015 |
| UA | 50333 U | 5/2010 |
| WO | 8603679 A1 | 7/1986 |
| WO | 9114759 A1 | 10/1991 |
| WO | 91017237 A1 | 11/1991 |
| WO | 9213520 A1 | 8/1992 |
| WO | 199325650 A1 | 12/1993 |
| WO | 9417783 A2 | 8/1994 |
| WO | 9502389 A2 | 1/1995 |
| WO | 9726854 A1 | 7/1997 |
| WO | 9823258 A1 | 6/1998 |
| WO | 9906010 A2 | 2/1999 |
| WO | 9918928 A1 | 4/1999 |
| WO | 9924004 A1 | 5/1999 |
| WO | 9924013 A1 | 5/1999 |
| WO | 9949837 A1 | 10/1999 |
| WO | 9957233 A1 | 11/1999 |
| WO | 0012553 A1 | 3/2000 |
| WO | 0032601 | 6/2000 |
| WO | 0119949 A1 | 3/2001 |
| WO | 0142409 A1 | 6/2001 |
| WO | 0148021 A1 | 7/2001 |
| WO | 2001076552 A2 | 10/2001 |
| WO | 2003051319 A1 | 6/2003 |
| WO | 03096998 A1 | 11/2003 |
| WO | 2004078901 A1 | 9/2004 |
| WO | 2005023975 A1 | 3/2005 |
| WO | 2008017540 A1 | 2/2008 |
| WO | 2008128826 A1 | 10/2008 |
| WO | 2008145582 A1 | 12/2008 |
| WO | 2009016555 A2 | 2/2009 |
| WO | 2009030594 A1 | 3/2009 |
| WO | 2009053931 A2 | 4/2009 |
| WO | 2010026009 A1 | 3/2010 |

(56) References Cited

FOREIGN PATENT DOCUMENTS

| | | | |
|---|---|---|---|
| WO | 2010052147 | A2 | 5/2010 |
| WO | 2012017091 | A2 | 2/2012 |
| WO | 2012052536 | A2 | 4/2012 |
| WO | 2012055587 | A1 | 5/2012 |
| WO | 2012055812 | A1 | 5/2012 |
| WO | 2012084970 | A1 | 6/2012 |
| WO | 2012127009 | A1 | 9/2012 |
| WO | 2012136651 | A1 | 10/2012 |
| WO | 2013010706 | A2 | 1/2013 |
| WO | 2013018805 | A1 | 2/2013 |
| WO | 2013119908 | A1 | 8/2013 |
| WO | 2014073245 | A1 | 5/2014 |
| WO | 2014073456 | A1 | 5/2014 |
| WO | 2014111667 | A2 | 7/2014 |
| WO | 2014111668 | A2 | 7/2014 |
| WO | 2014148245 | A1 | 9/2014 |
| WO | 2015067779 | A1 | 5/2015 |
| WO | 2015085376 | A1 | 6/2015 |
| WO | 2015122371 | A1 | 8/2015 |
| WO | 2015141787 | A1 | 9/2015 |
| WO | 2016049389 | A1 | 3/2016 |
| WO | 2016147196 | A1 | 9/2016 |
| WO | 2017052161 | A1 | 3/2017 |
| WO | 2017140798 | A1 | 8/2017 |
| WO | 2017140802 | A1 | 8/2017 |
| WO | 2017207685 | A1 | 12/2017 |
| WO | 2018023180 | A1 | 2/2018 |
| WO | 2018109148 | A1 | 6/2018 |
| WO | 2019030458 | A2 | 2/2019 |
| WO | 2019074990 | A1 | 4/2019 |
| WO | 2019074992 | A1 | 4/2019 |
| WO | 2019200027 | A1 | 10/2019 |
| WO | 2020005309 | A1 | 1/2020 |
| WO | 2020030732 | A1 | 2/2020 |
| WO | 2021026572 | A1 | 2/2021 |
| WO | 2021099088 | A1 | 5/2021 |
| WO | 2021127318 | A1 | 6/2021 |
| WO | 2021231510 | A1 | 11/2021 |

OTHER PUBLICATIONS

PCT Search Report and Written Opinion for PCT/US2022/028255 dated Sep. 19, 2022, 16 pages.
"Personal care solutions Guide", Solvay, Publication date: May 2018, 84 pages.
Product Data Record Tego®Betain F KB 5, dated Jul. 1, 2015, 4 pages.
"Anti-Dandruff Shampoo", Mintel Database, Record No. 752198, dated Aug. 2007; pp. 1-3.
"Dandruff Control Shampoo", Mintel Database, Record No. 2300131, dated Jan. 2014; pp. 1-2.
"Foam & chemical contamination in waterways", Retrieved From https://www.epa.nsw.gov.au/-/media/epa/corporate-site/resources/epa/foam-chemical-contamination-in-waterway.pdf, Dec. 2015, 2 Pages.
"Natural Detangling Shampoo", Mintel Database, dated Sep. 13, 2017; 2 pages.
"Soda Shampoo", Mintel Database, dated Apr. 2015; pp. 1-4.
"Treatment Foam for Recurrent Scaling Conditions", Mintel Database, Aug. 2007; pp. 1-2.
Acne Foaming Cleanser, Database accession No. 4172863, Jul. 29, 2016, 3 pages.
Air Quality of the Iowa Department of Natural Resources. A Review of The Science and Technology of Odor Measurement, 2005, 51 pages (2005).
Anonymous: "MERQUAT Polyquaternium 47 Series, Water Soluble Polymers for Personal Care", Jul. 30, 2017, URL: https://www.in-cosmetics.com/_novadocuments/2729, retrieved on Dec. 21, 2018; 1 page.
Anonymous: "Naturally Derived Body Wash", Database GNPD [Online] MINTEL; Feb. 15, 2021, 2 pages.
Anonymous: "Peptide Shampoo", Database GNPD [Online] MINTEL; Dec. 14, 2015, 3 pages.
Anonymous: "Replenishing Moisture Shampoo", Database GNPD [Online] MINTEL, Mar. 10, 2015br.
Anonymous: "Shampoo", Database GNPD [Online] MINTEL, Jan. 26, 2021, 3 pages.
ANONYMOUS: "Shampooing au Phytolait d'abricot—Formule N°102-MP06-MI3-AA03", Internet Citation, Feb. 19, 2005, Retrieved from the Internet:URL: http://web.archive.org/web/20050219040350/www.albanmuller.com/francais/catalogue/formules/formul10.asp, 1 page.
ASTM D3954-94, Reapproved 2010, vol. 15.04, Standard Test Method for Dropping Point of Waxes.
BASF, "Practical Guide to Rheology Modifiers", download from https://insights.basf.com/files/BASF_ED_RheologyModifiers_download.pdf on Nov. 1, 2022. (Year: 2022).
Brattoli et al. Odour Detection Methods: Olfactometry and Chemical Sensors. Sensors (Basel), 2011; 11(5); 5290-5322 (2011).
Carbopol Aqua SF-1 Polymer Technical Data Sheet, TDS-294, dated Dec. 2000; pp. 1-9.
Chemical Book (Chemical Book, Isolongifolone, available at http://www.chemicalbook.com/ProductChemicalPropertiesCB5318980_EN.htm), no date available.
Christensen et al., "Experimental Determination of Bubble Size Distribution in a Water Column by Interferometric Particle Imaging and Telecentric Direct Image Method", Student Report, Aalborg University; dated Jun. 3, 2014; 123 pages.
Crepaldi, E.L., et al., Chemical, Structural, and Thermal Properties of Zn(II)—Cr(III) Layered Double Hydroxides Intercalated with Sulfated and Sulfonated Surfactants, Journal of Colloid and Interface Science, 2002, pp. 429-442, vol. 248.
D'Souza et al., Shampoo and Conditioners: What a Dermatologist Should Know? Indian J Dermatol, dated May-Jun. 2015; pp. 60(3), 248-254 (2015).
Database GNPD [Online] MINTEL;Mar. 28, 2018 (Mar. 28, 2018),anonymous: Dandruff Control Shampoo 11,XP055787038,Database accession No. 5556267abstract.
Database GNPD [Online] MINTEL;Apr. 5, 2005 (Apr. 5, 2005),anonymous: "Anticaspa-Graso Anti-DandruffShampoo",XPC:155787029,Database accession No. 351776paragraph [ingredients].
Database GNPD [Online] MINTEL; Jan. 6, 2020 (Jan. 6, 2020),anonymous: 11 Shampoo 11, 3 pages.
Database WPI; Week 201459; Thomson scientific, London, GB; AN 2014-P66521; XP002752638.
Datasheet: Empigen Total Active TC/U, Datasheet, dated Jan. 31, 2017 (Innospec); 2 pages.
Dehyquart Guar: Published dated Nov. 2010; pp. 1-34.
Fevola, Michael J. "Guar Hydroxypropyltrimonium Chloride." Cosmetics and toiletries; vol. 127.1; Jan. 2012; pp. 16-21.
Grillet et al., "Polymer Gel Rheology and Adhesion", Rheology, 2012, pp. 59-80.
Hair Care/Conditioning Polymers Differentiation, Anonymous, Feb. 1, 2017, URL: http://www.biochim.it./assets/site/media/allegati/cosmetica/hair-care/tab-merquat-hair-care.pdf, retrieved on Dec. 20, 2018; p. 1.
Happi: "Sulfate-Free Surfactants Conditioning Shampoo", Retrieved from the Internet:URL:https://www.happi.com/contents/view_formulary/2009-10-01/sulfate-free-surfactants-conditioning-shampoo/, XP002804301, Jan. 10, 2019, 1 page.
Inspection certificate for Hostapon® CCG, Clariant Ibérica Production, S.A., May 6, 2019; p. 1-2.
McGinley et al. American Association of Textile Chemists and Colorists, 2017, 17 pages, (2017).
McGinley et al. Performance Verification of Air Freshener Products and Other Odour Control Devices for Indoor Air Quality Malodours. Presented at the 8th Workshop on Odour and Emissions of Plastic Materials Universitat Kassel Institut for Wesrkstofftechnik Kassel, Germany, Mar. 27-28, 2006, 13 pages.
Medvedev, Diffusion Coefficients in Multicomponent Mixtures, PhD Thesis from Technical University of Denmark, dated 2005, 181 pages.

(56) References Cited

OTHER PUBLICATIONS

Mintel GNPD Base, Bright Blonde Shampoo Record No. 3412889 Feb. 29, 2016; 2 pages.
Mintel GNPD Base, Mineral Conquer Blonde Silver Shampoo Record No. 3953107 Apr. 30, 2016; 2 pages.
Mintel GNPD Base, Royal Treatment Collection, Record No. 1946223 dated Dec. 31, 2011, 3 pages.
Morioka, H et al. "Effects of Zinc on the New Preparation Method of Hydroxy Double Salts" Inorg. Chem. 1999, 38, 4211-6.
Musazzi, "Emulsion versus nonoemulsion: how much is the formulative shift critical for a cosmetic product?" (Drug Deliv. and Trans. Res. (2018) 8: pp. 414-421 (Year: 2018).
Natural oils: why specific carbon chains are chosen for certain surfactant properties, Chemlink, URL Link: https://www.chemlink.co.uk/natural-oils-why-specific-carbon-chains-are-chosen-for-certain-surfactant-properties/a (Year: 2022), 4 pgs.
Naturally Rich Moisturizing Shampoo, Database accession No. 6421011, Mar. 27, 2019, 3 pages.
Noritomi H. Formation and Solubilization Property of Water-in-Oil Microemulsions of Alkyl Glucoisdes. Advances in Nanoparticles, 2013, 2, 366-371 (Year: 2013).
Parchem fine & specialty chemicals. MIPA-laureth sulfate supplier distributor—CAS 83016-76-6; dated 2021; pp. 1-7.
PERM Inc,, Diffusion Coefficient: Measurement Techiques, https://perminc.com/resources/fundamentals-of-fluid-flow-in-porous-media/chapter-3-molecular-diffusion/diffusion-coefficient/measurement-techniques, dated Oct. 2020; p. 1-4.
Polyquaternium: "Final Report on the Safety Assessment of the Polyquaternium-10", Journal of the American College of Toxicology, Jan. 1, 1988, URL: http://www.beauty-review.nl/wp-content/uploads/2015/02/Final-Report-on-the Safety-Assessment-of-Polyquaternium-10.pdf, retrieved on Dec. 20, 2018; 9 pages.
Practical Modern Hair Science, Published 2012; 43 pages.
Product Bulletin, Amphosol® CG, Cocamidopropyl Betaine, Stepan Company, Jun. 2011; 1-2 pages.
Product Data Sheet for Chemory™ LS Surfactant, Sodium Lauroyl Sarcosinate, Lubrizol Advanced Materials, Inc., Mar. 24, 2020; 1-2 pages.
Product Data Sheet, Eversoft™ UCS-40S, Disodium Cocoyl Glutamate (Sodium Cocoyl Glutamate*), Sino Lion USA, Jul. 2018; 2 pages.
Product Fact Sheet—Hostapon® CCG, mild anionic surfactant for the cosmetic industry, Clariant International Ltd., Aug. 2014; 1-3 pages.
Product Fact Sheet, Hostapon® CGN, Mild anionic surfactant for the cosmetic industry, Clariant International Ltd., Jan. 2016; 1-2 pages.
Rajendran A. et al: "Study on the Analysis of Trace Elements in Aloe veraand Its Biological Importance Study on the Analysis of Trace Elements in Aloe vera and Its Biological Importance", Journal of Applied Sciences Research, Jan. 1, 2007 (Jan. 1, 2007), XP055799133, pp. 1476-1478.
Robinson et al., Final Report of the Amended Safety Assessment of Sodium Laureth Sulfate and Related Salts of SulfatedEthoxylated Alcohols, International Journal of Toxicology 29 (Supplement 3); dated 2010; pp. 151S-161S.
S. Herrwerth et al.: "Highly Concentrated Cocamidopropyl Betaine—The Latest Developments for Improved Sustainability and Enhanced Skin Care", Tenside, Surfactants, Detergents, vol. 45, No. 6, dated Nov. 1, 2008, pp. 304-308, p. 305—left-hand column; 3 pages.
Safety assessment of amino acid alkyl amides used in cosmetics, dated Sep. 20, 2013, 46 pages.
Schaefer, Katie, "Eco-friendly, Non-flammable Liquified Gas Propellant", https://www.cosmeticsandtoiletries.com/formulating/function/aids/13848589.html#close-olytics.modal. Published Jan. 30, 2012; 1-2 pages.
Sensory.,"A Review of the Science and Technology of Odor Measurement", Prepared for the Air Quality Bureau of the Iowa Department of Natural Resources, Dec. 30, 2005 51 pages.
Shampoo C, Database accession No. 1632217, Sep. 29, 2011, 3 pages.
Softazoline CL-R, Kawaken Singapore PTE Ltd. Website printout from http://kawaken.com.kg/softazoline-ch-r//a, accessed on Nov. 30, 2022.
Todd et al., Volatile Silicone Fluids for Cosmetics, Cosmetics and Toiletries, vol. 91, pp. 27-32 (Jan. 1976).
UL Prospector® Product Data Sheet, Plantacare® 818 UP, C8-16 fatty alcohol glucoside, BASF, dated May 21, 2015; 1-3 pages.
Unhale Shrikrushna Subhash et al: Formulation and Development of Sulphate Free Shampoo About an Updates andGuidelines of Corona Virus View project health and beauty science View project Rohit Bhavsar Reliance Industries Limited; International Journal for Research inApplied Science & Engineering Technology,Apr. 1, 2020 (Apr. 1, 2020)t XP055842327, DOI: 10.22214, 14 pages.
"Deep Image Matting", Ning Xu et al, Beckman Institute for Advanced Science and Technology, University of Illinois at Urbana-Champaign, Adobe Research, dated Mar. 10, 2017; 10 pages.
"Comparative Study on the Chemical constituents of Aloe Vera and Aloe Kula in China ", Zhang Xiaohua et al., Flavor Cosmetics, No. 63, dated Dec. 31, 2000, pp. 7-11.
PubChem CID 3033856 for decyl glucoside. downloaded Jun. 22, 2023, 32 pages. (Year: 2023).

* cited by examiner

SHAMPOO COMPOSITION

FIELD

The present disclosure relates to mild shampoo compositions comprising alkyl polyglucoside, sclerotium gum, and a cationic polymer which deliver consumer desired wet conditioning and adequate viscosity for ease of use.

BACKGROUND

Human hair becomes soiled due to contact with the surrounding environment and from sebum secreted by the scalp. Soiled hair has a dirty feel and an unattractive appearance. Application and washing of the soiled hair with a shampoo composition can restore hair to a clean and attractive appearance by removing oil and other soils from the hair. Known shampoo compositions typically remove oil and soil from hair with anionic surfactants. Shampoos including anionic surfactants, however, may result in a number of undesirable characteristics such as poor quality of hair feel. Cationic polymers are commonly used in anionic surfactant cleansing compositions to provide moisturization and wet detangle to hair. Non-ionic surfactants are known for mildness on skin but are also known to be difficult to use in combination with charged polymers (cationic polymers) resulting in an unstable composition. Additionally, non-ionic surfactant systems are typically thin (low viscosity) and may need a thickening polymer to increase viscosity to prevent solution dripping off consumers hands prior to application to hair. However, the combination of cationic polymer and a commonly used thickener such as guar gum typically results in an unstable composition. Surprisingly, it has been found that sclerotium gum with the unique triple helix structure is able to stabilize cationic polymer to achieve a single-phase stable cleansing composition delivering a range of desired wet conditioning benefit and desired viscosity.

It is desirable to have a shampoo composition that cleans without the use of anionic surfactants and also results in good in use physical properties, while also delivering the desired hair benefits. Surprisingly, it has been found that a shampoo composition comprising a nonionic surfactant alkyl polyglucoside, sclerotium gum, and a cationic polymer is phase stable and delivers consumer desired wet conditioning and adequate viscosity for ease of use.

SUMMARY

A shampoo composition comprising 5 wt % to 35 wt % of alkyl polyglucoside; 0.15 wt % to 1.05% sclerotium gum, and 0.15 wt % to 1.05% of a cationic polymer, wherein the shampoo composition has a viscosity of 0.6 Pa-s to 20 Pa-s, and wherein the shampoo composition comprises less than 1 wt % ionic surfactant.

DETAILED DESCRIPTION

Figure 1:
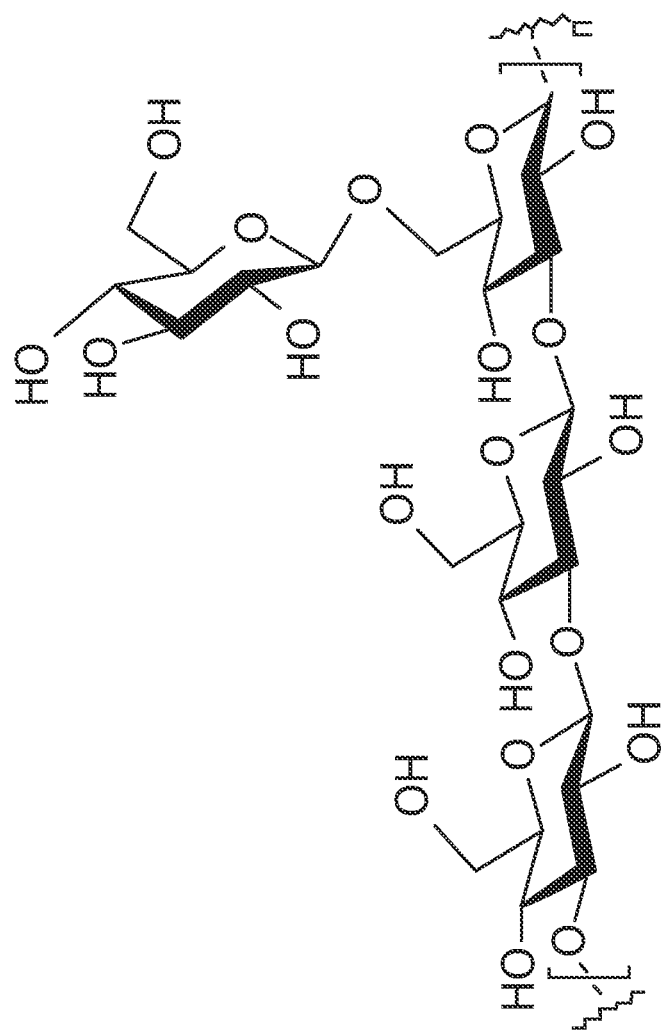
FIG. 1 illustrates an examples of a typical sclerotium gum structure.

While the specification concludes with claims which particularly point out and distinctly claim the invention, it is believed the present disclosure will be better understood from the following description.

Definitions

In all embodiments of the present disclosure, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under one atmosphere of pressure and at 50% relative humidity. All such weights as they pertain to listed ingredients are based on the active level and do not include carriers or by-products that may be included in commercially available materials, unless otherwise specified.

As used herein, "molecular weight" or "Molecular weight" refers to the weight average molecular weight unless otherwise stated. Molecular weight is measured using industry standard method, gel permeation chromatography ("GPC").

The term "charge density," as used herein, refers to the ratio of the number of positive charges on a polymer to the molecular weight of said polymer.

The term "comprising," as used herein, means that other steps and other ingredients which do not affect the end result can be added. This term encompasses the terms "consisting of" and "consisting essentially of." The compositions and methods/processes of the present disclosure can comprise, consist of, and consist essentially of the elements and limitations of the invention described herein, as well as any of the additional or optional ingredients, components, steps, or limitations described herein.

The term "polymer," as used herein, includes materials whether made by polymerization of one type of monomer or made by two (i.e., copolymers) or more types of monomers.

The term "suitable for application to human hair," as used herein, means that the personal care compositions or components thereof, are acceptable for use in contact with human hair and the scalp and skin without undue toxicity, incompatibility, instability, allergic response, and the like.

The term "water soluble," as used herein, means that the material is soluble in water. The material can be soluble at 25° C. at a concentration of 0.1% by weight of the water solvent, at 1% by weight of the water solvent, at 5% by weight of the water solvent, and at 15% or more by weight of the water solvent.

The terms "sulfate free" and "substantially free of sulfates" means essentially free of sulfate-containing compounds except as otherwise incidentally incorporated as minor components. The term "sulfated surfactants" means surfactants which contain a sulfate group. The term "substantially free of sulfated surfactants" means essentially free of surfactants containing a sulfate group except as otherwise incidentally incorporated as minor components.

Shampoo Composition

The shampoo composition as described herein provides consumer desired hair conditioning feel, and the shampoo composition is stable and has a viscosity which delivers a good in use experience. The shampoo composition comprises a nonionic surfactant such as an alkyl polyglucoside. The shampoo composition further comprises sclerotium gum, and a cationic polymer. This composition remains phase stable and has good viscosity and continues to provide desired lather for cleaning, quick rinse and clean hair feel. Suitable viscosity of the shampoo composition is 0.6 Pa-s to 20 Pa-S, 0.7 Pa-s to 18 Pa-s, 0.8 Pa-s to 18 Pa-s, and 1.0 Pa-s to 16 Pa-s.

The shampoo composition is substantially free of ionic surfactant, including sodium alkyl sulfate, sodium cocoyl isethionate, sodium lauroyl sarcosinate, cocamidopropyl betaine, sodium lauroamphoacetate, cetyltrimethylammonium chloride, behenyltrimethylammonium chloride and mixtures thereof. As used herein, substantially free of ionic surfactant means comprises less than 1 wt %, 0 wt % to 1 wt %, 0 wt % to 0.5 wt %, 0.1 wt % to 0.2 wt %, and alternatively 0 wt % to 0.3 wt % of ionic surfactant.

Non-Ionic Surfactant

The shampoo composition comprises 5% to 35% of the non-ionic surfactant alkyl polyglucoside. The shampoo composition comprises 5 wt % to 35 wt % of alkyl polyglucoside, 5 wt % to 25 wt % of alkyl polyglucoside, 7 wt % to 20 wt % of alkyl polyglucoside, and any combination thereof. The non-ionic surfactant can be a polyglucoside selected from decyl glucoside, caprylyl glucoside, caprylyl/capryl glucoside, undecyl glucoside, octyl glucoside, and mixtures thereof.

The non-ionic surfactant can be an alkyl polyglucoside having the structure:

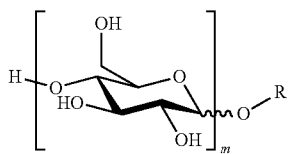

where "R" is an alkyl or alkenyl group having 8 to 20 carbons, and "m" is degree of polymerization of from 1 to 5. Alternatively, the R is from 8 to 16 carbons, and alternatively wherein the R is from 8 to 12 carbons.

The non-ionic surfactant can be a decyl glucoside having the structure:

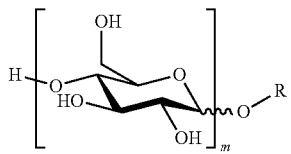

where R is a C10 alkyl or alkenyl group and the degree of polymerization (m) is 1.

Sclerotium Gum

The shampoo composition comprises 0.15 wt % to 1.05 wt % sclerotium gum, 0.15 wt % to 1.0 wt % sclerotium gum, 0.2 wt % to 0.8 wt % sclerotium gum, 0.4 wt % to 0.8 wt % sclerotium gum, and/or 0.4 wt % to 0.6 wt % sclerotium gum, and any combination thereof. Sclerotium gum is also called scleroglucan, and it is a branched polysaccharide. In some instances, the primary structure of the scleroglucan consists of glucose molecules linked by β-(1,3) linkage, and every third glucose molecule in the primary structure contains an additional glucose molecule linked by a β-(1,6) linkage. In certain solutions, scleroglucan forms a triple helix shape.

Figure 2:
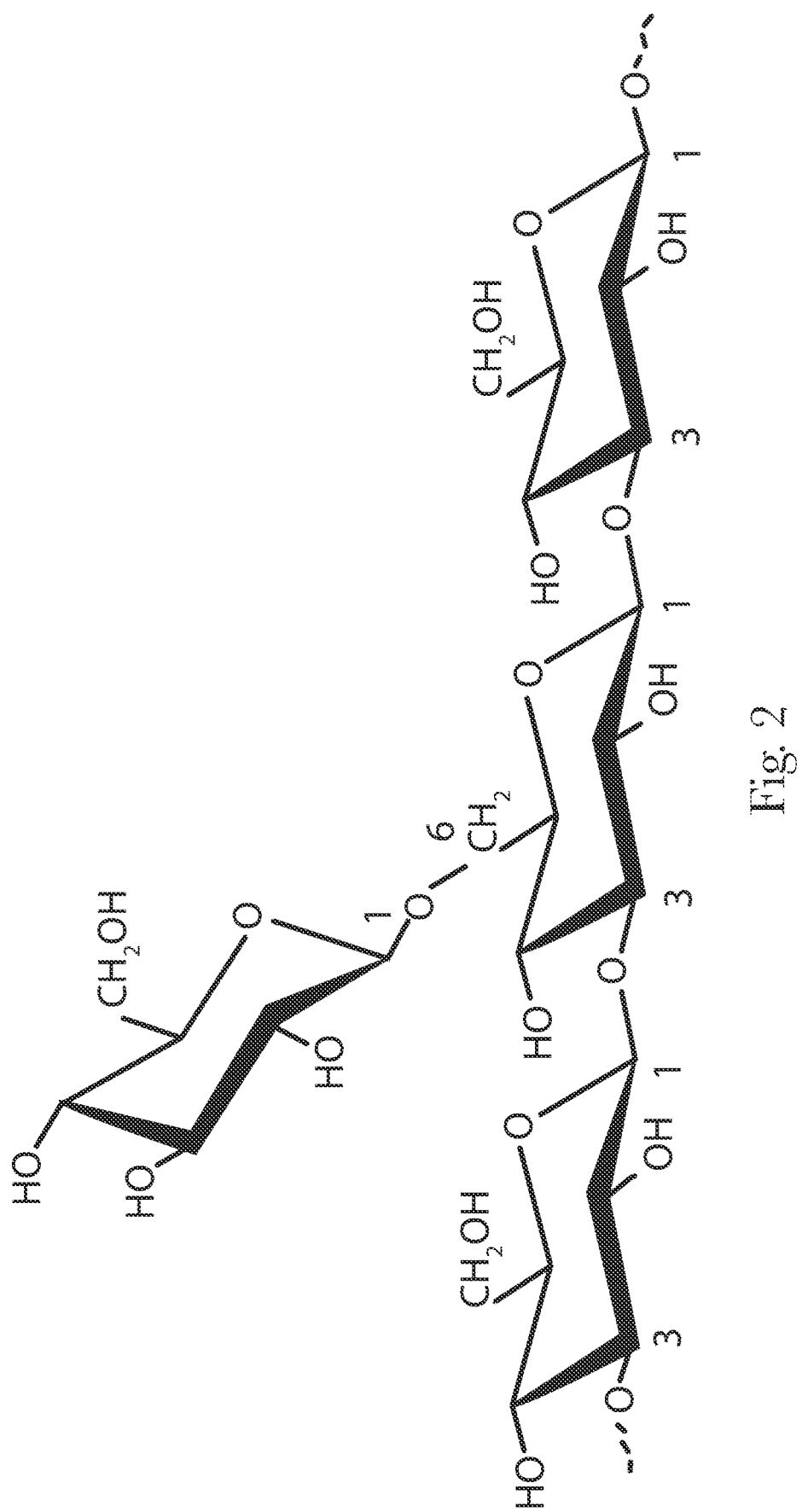
FIG. 2 illustrates an example of a β-(1,3)-β(1,6) glucan structure exhibiting the (3:1) side branching ratio of scleroglucan.
Figure 3:
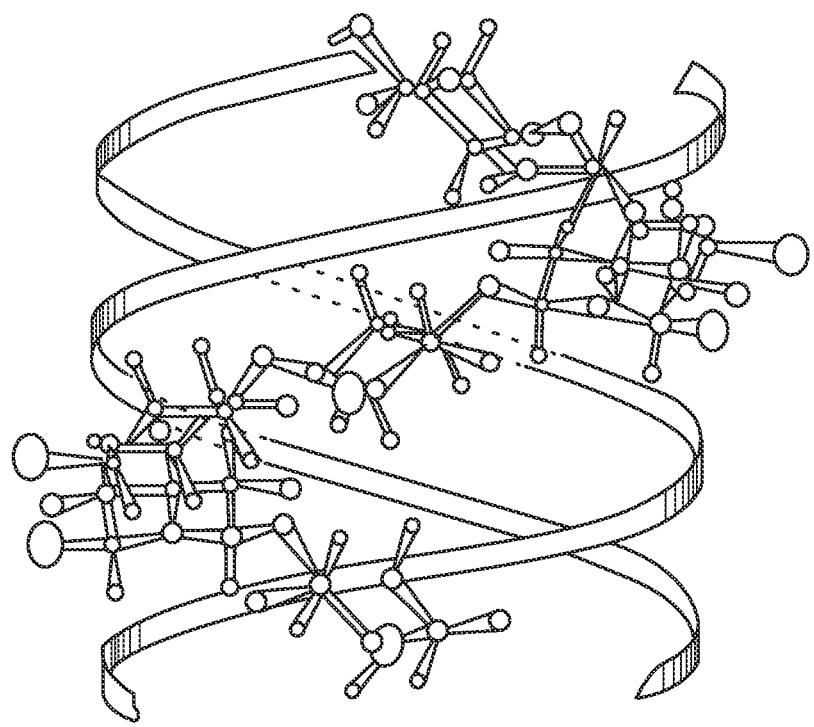
FIG. 3 illustrates an example of a tridimensional conformation of a scleroglucan triplex.

FIG. 1 shows an example of a typical sclerotium gum structure. FIG. 2 shows an example of a β-(1,3)-β-(1,6) glucan structure exhibiting the (3:1) side branching ratio of scleroglucan (Martin et al., 2007). FIG. 3 shows an example of a tridimensional conformation of a scleroglucan triplex (Crescenzi et al., 1988). Specific examples of sclerotium gum include Amigum ER commercially available from Alban Muller and Actigum CS 11 QD commercially available from Cargill.

Cationic Polymer

A shampoo composition can include a cationic polymer for wet conditioning benefits. Suitable cationic polymers can include: (a) a cationic guar polymer, (b) a cationic non-guar galactomannan polymer, (c) a cationic starch polymer, (d) a cationic copolymer of acrylamide monomers and cationic monomers, (e) a synthetic, non-crosslinked, cationic polymer, which may or may not form lyotropic liquid crystals upon combination with the detersive surfactant, and (f) a cationic cellulose polymer. In certain examples, more than one cationic polymer can be included.

A cationic polymer can be included by weight of the shampoo composition at 0.05% to 3%, 0.075% to 2.0%, or at 0.1% to 1.0%. Cationic polymers can have cationic charge densities of 0.9 meq/g or more, 1.2 meq/g or more, and 1.5 meq/g or more. However, cationic charge density can also be 7 meq/g or less and alternatively 5 meq/g or less. The charge densities can be measured at the pH of intended use of the shampoo composition. (e.g., at pH 3 to pH 9; or pH 4 to pH 8). The average molecular weight of cationic polymers can generally be between 10,000 and 10 million, between 50,000 and 5 million, and between 100,000 and 3 million, and between 100,000 and 2.5 million. Low molecular weight cationic polymers can be used. Low molecular weight cationic polymers can have greater translucency in the liquid carrier of a shampoo composition. The cationic polymer can be a single type, such as the cationic guar polymer guar hydroxypropyltrimonium chloride having a weight average molecular weight of 2.5 million g/mol or less, and the shampoo composition can be substantially free of additional cationic polymers. As used herein, substantially free of additional cationic polymers means 0 to 0.05 of an additional cationic polymer.

Cationic Guar Polymer

The cationic polymer can be a cationic guar polymer, which is a cationically substituted galactomannan (guar) gum derivative. Suitable guar gums for guar gum derivatives can be obtained as a naturally occurring material from the seeds of the guar plant. As can be appreciated, the guar molecule is a straight chain mannan which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums can be obtained through reactions between the hydroxyl groups of the polygalactomannan and reactive quaternary ammonium compounds. The degree of substitution of the cationic groups onto the guar structure can be sufficient to provide the requisite cationic charge density described above.

A cationic guar polymer can have a weight average molecular weight ("M.Wt.") of less than 2.5 million g/mol, and can have a charge density 0.05 meq/g to 2.5 meq/g. Alternatively, the cationic guar polymer can have a weight average M.Wt. of less than 1.5 million g/mol, 150 thousand g/mol to 1.5 million g/mol, 200 thousand g/mol to 1.5 million g/mol, 300 thousand g/mol to 1.5 million g/mol, and 700,000 thousand g/mol to 1.5 million g/mol. The cationic guar polymer can have a charge density 0.2 meq/g to 2.2 meq/g, 0.3 meq/g to 2.0 meq/g, 0.4 meq/g to 1.8 meq/g; and 0.5 meq/g to 1.7 meq/g.

A cationic guar polymer can have a weight average M.Wt. of less than 1 million g/mol, and can have a charge density 0.1 meq/g to 2.5 meq/g. A cationic guar polymer can have a weight average M.Wt. of less than 900 thousand g/mol, 150 thousand to 800 thousand g/mol, 200 thousand g/mol to 700 thousand g/mol, 300 thousand to 700 thousand g/mol, 400 thousand to 600 thousand g/mol, 150 thousand to 800 thousand g/mol, 200 thousand g/mol to 700 thousand g/mol, 300 thousand g/mol to 700 thousand g/mol, and 400 thousand g/mol to 600 thousand g/mol. A cationic guar polymer has a charge density 0.2 meq/g to 2.2 meq/g, 0.3 meq/g to 2.0 meq/g, 0.4 meq/g to 1.8 meq/g; and 0.5 meq/g to 1.5 meq/g.

A shampoo composition can include 0.01% to less than 0.7%, by weight of the shampoo composition of a cationic guar polymer, 0.04% to 0.55%, by weight, 0.08% to 0.5%, by weight, 0.16% to 0.5%, by weight, 0.2% to 0.5%, by weight, 0.3% to 0.5%, by weight, and 0.4% to 0.5%, by weight.

The cationic guar polymer can be formed from quaternary ammonium compounds which conform to general Formula II:

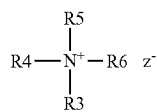
(II)

where $R^3$, $R^4$ and $R^5$ are methyl or ethyl groups, and $R^6$ is either an epoxyalkyl group of the general Formula III:

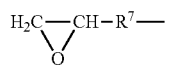
(III)

or $R^6$ is a halohydrin group of the general Formula IV:

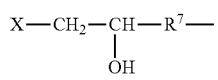
(IV)

wherein $R^7$ is a $C_1$ to $C_3$ alkylene; X is chlorine or bromine, and Z is an anion such as Cl—, Br—, I— or $HSO_4^-$.

Suitable cationic guar polymers can conform to the general formula V:

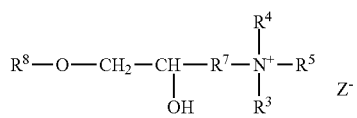
(V)

wherein $R^8$ is guar gum; and wherein $R^4$, $R^5$, $R^6$ and $R^7$ are as defined above; and wherein Z is a halogen.

Suitable cationic guar polymers can conform to Formula VI:

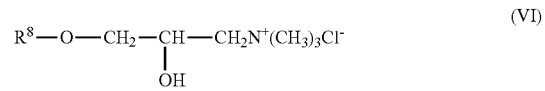
(VI)

wherein $R^8$ is guar gum.

Suitable cationic guar polymers can also include cationic guar gum derivatives, such as guar hydroxypropyltrimonium chloride. Suitable examples of guar hydroxypropyltrimonium chlorides can include the Jaguar® series commercially available from Solvay S.A., Hi-Care Series from Rhodia, and N-Hance and AquaCat from Ashland Inc. Jaguar® C-500 has a charge density of 0.8 meq/g and a M.Wt. of 500,000 g/mole; Jaguar® C-17 has a cationic charge density of 0.6 meq/g and a M.Wt. of 2.2 million g/mol; Jaguar® C 13S has a M.Wt. of 2.2 million g/mol and a cationic charge density of 0.8 meq/g; Hi-Care 1000 has a charge density of 0.7 meq/g and a M.Wt. of 600,000 g/mole; N-Hance 3269 and N-Hance 3270, have a charge density of 0.7 meq/g and a M.Wt. of 425,000 g/mole; N-Hance 3196 has a charge density of 0.8 meq/g and a M.Wt. of 1,100,000 g/mole; and AquaCat CG518 has a charge density of 0.9 meq/g and a M.Wt. of 50,000 g/mole. N-Hance BF-13 and N-Hance BF-17 are borate (boron) free guar polymers. N-Hance BF-13 has a charge density of 1.1 meq/g and M.W.t of 800,000 and N-Hance BF-17 has a charge density of 1.7 meq/g and M.W.t of 800,000.

Cationic Non-Guar Galactomannan Polymer

The cationic polymer can be a galactomannan polymer derivative. Suitable galactomannan polymer can have a mannose to galactose ratio of greater than 2:1 on a monomer-to-monomer basis and can be a cationic galactomannan polymer derivative or an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers can be present in the endosperm of seeds of the Leguminosae family Galactomannan polymers are made up of a combination of mannose monomers and galactose monomers. The galactomannan molecule is a straight chain mannan branched at regular intervals with single membered galactose units on specific mannose units. The mannose units are linked to each other by means of β (1-4) glycosidic linkages. The galactose branching arises by way of an α (1-6) linkage. The ratio of mannose monomers to galactose monomers varies according to the species of the plant and can be affected by climate. Non-guar galactomannan polymer derivatives can have a ratio of mannose to galactose of greater than 2:1 on a monomer to monomer basis. Suitable ratios of mannose to galactose can also be greater than 3:1 or greater than 4:1. Analysis of mannose to galactose ratios is well known in the art and is typically based on the measurement of the galactose content.

The gum for use in preparing the non-guar galactomannan polymer derivatives can be obtained from naturally occurring materials such as seeds or beans from plants. Examples of various non-guar galactomannan polymers include Tara gum (3 parts mannose/1 part galactose), Locust bean or Carob (4 parts mannose/1 part galactose), and Cassia gum (5 parts mannose/1 part galactose).

A non-guar galactomannan polymer derivative can have a M. Wt. 1,000 g/mol to 10,000,000 g/mol, and a M.Wt. 5,000 g/mol to 3,000,000 g/mol.

The shampoo compositions described herein can include galactomannan polymer derivatives which have a cationic charge density 0.5 meq/g to 7 meq/g. The galactomannan polymer derivatives can have a cationic charge density 1 meq/g to 5 meq/g. The degree of substitution of the cationic groups onto the galactomannan structure can be sufficient to provide the requisite cationic charge density.

A galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general Formulas II to VI, as defined above.

Cationic non-guar galactomannan polymer derivatives formed from the reagents described above can be represented by the general Formula VII:

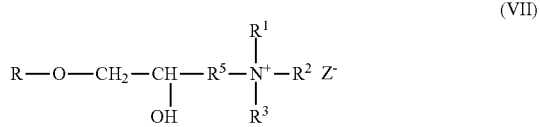

(VII)

wherein R is the gum. The cationic galactomannan derivative can be a gum hydroxypropyltrimethylammonium chloride, which can be more specifically represented by the general Formula VIII:

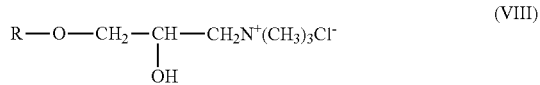

(VIII)

The galactomannan polymer derivative can be an amphoteric galactomannan polymer derivative having a net positive charge, obtained when the cationic galactomannan polymer derivative further comprises an anionic group.

A cationic non-guar galactomannan can have a ratio of mannose to galactose which is greater than 4:1, a M.Wt. of 100,000 g/mol to 500,000 g/mol, a M.Wt. of 50,000 g/mol to 400,000 g/mol, and a cationic charge density 1 meq/g to 5 meq/g, and 2 meq/g to 4 meq/g.

Shampoo compositions can include at least 0.05% of a galactomannan polymer derivative by weight of the composition. The shampoo compositions can include 0.05% to 2%, by weight of the composition, of a galactomannan polymer derivative.

Cationic Starch Polymers

Suitable cationic polymers can also be water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The shampoo compositions described herein can include cationically modified starch polymers at a range of 0.01% to 10%, and/or 0.05% to 5%, by weight of the composition.

The cationically modified starch polymers disclosed herein have a percent of bound nitrogen of 0.5% to 4%.

The cationically modified starch polymers can have a molecular weight 850,000 g/mol to 15,000,000 g/mol and 900,000 g/mol to 5,000,000 g/mol.

Cationically modified starch polymers can have a charge density of 0.2 meq/g to 5 meq/g, and 0.2 meq/g to 2 meq/g. The chemical modification to obtain such a charge density can include the addition of amino and/or ammonium groups into the starch molecules. Non-limiting examples of such ammonium groups can include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. Further details are described in Solarek, D. B., Cationic Starches in Modified Starches: Properties and Uses, Wurzburg, O. B., Ed., CRC Press, Inc., Boca Raton, Fla. 1986, pp 113-125 which is hereby incorporated by reference. The cationic groups can be added to the starch prior to degradation to a smaller molecular weight or the cationic groups may be added after such modification.

A cationically modified starch polymer can have a degree of substitution of a cationic group 0.2 to 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution can be determined using proton nuclear magnetic resonance spectroscopy ("$^1$H NMR") methods well known in the art. Suitable $^1$H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be selected from a variety of sources such as tubers, legumes, cereal, and grains. For example, starch sources can include corn starch, wheat starch, rice starch, waxy corn starch, oat starch, cassava starch, waxy barley, waxy rice starch, glutenous rice starch, sweet rice starch, amioca, potato starch, tapioca starch, oat starch, sago starch, sweet rice, or mixtures thereof. Suitable cationically modified starch polymers can be selected from degraded cationic maize starch, cationic tapioca, cationic potato starch, and mixtures thereof. Cationically modified starch polymers are cationic corn starch and cationic tapioca.

The starch, prior to degradation or after modification to a smaller molecular weight, can include one or more additional modifications. For example, these modifications may include cross-linking, stabilization reactions, phosphorylations, and hydrolyzations. Stabilization reactions can include alkylation and esterification.

Cationically modified starch polymers can be included in a shampoo composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

The starch can be readily soluble in water and can form a substantially translucent solution in water. The transparency of the composition is measured by Ultra-Violet/Visible ("UV/VIS") spectrophotometry, which determines the absorption or transmission of UV/VIS light by a sample, using a Gretag Macbeth Colorimeter Color. A light wavelength of 600 nm has been shown to be adequate for characterizing the degree of clarity of shampoo compositions.

Cationic Copolymer of an Acrylamide Monomer and a Cationic Monomer

A shampoo composition can include a cationic copolymer of an acrylamide monomer and a cationic monomer, wherein the copolymer has a charge density of 1.0 meq/g to 3.0 meq/g. The cationic copolymer can be a synthetic cationic copolymer of acrylamide monomers and cationic monomers.

Suitable cationic polymers can include:
(i) an acrylamide monomer of the following Formula IX:

(IX)

where $R^9$ is H or $C_{1-4}$ alkyl; and $R^{19}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$ cycloalkyl; and
(ii) a cationic monomer conforming to Formula X:

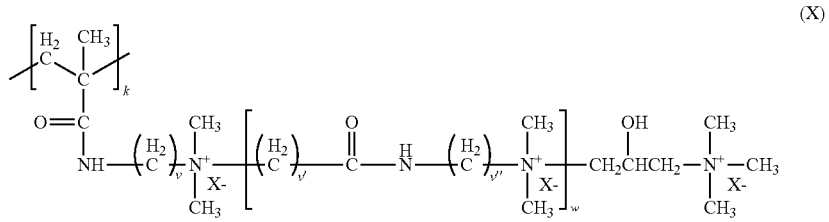

(X)

where k=1, each of v, v', and v" is independently an integer of from 1 to 6, w is zero or an integer of from 1 to 10, and $X^-$ is an anion.

A cationic monomer can conform to Formula X where k=1, v=3 and w=0, z=1 and $X^-$ is $Cl^-$ to form the following structure (Formula XI):

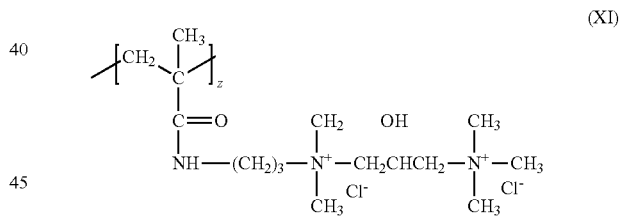

(XI)

As can be appreciated, the above structure can be referred to as diquat.

A cationic monomer can conform to Formula X wherein v and v" are each 3, v'=1, w=1, y=1 and $X^-$ is $Cl^-$, to form the following structure of Formula XII:

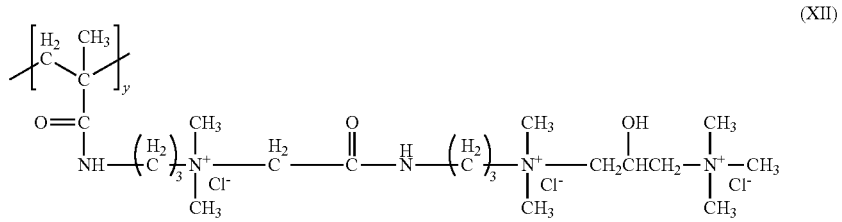

(XII)

The structure of Formula XII can be referred to as triquat.

The acrylamide monomer can be either acrylamide or methacrylamide.

The cationic copolymer can be AM:TRIQUAT which is a copolymer of acrylamide and 1,3-Propanediaminium,N-[2-[[[dimethyl[3-[(2-methyl-1-oxo-2-propenyl)amino]propyl] ammonio]acetyl]amino]ethyl]2-hydroxy-N,N,N',N'-pentamethyl-, trichloride. AM:TRIQUAT is also known as polyquaternium 76 (PQ76). AM:TRIQUAT can have a charge density of 1.6 meq/g and a M.Wt. of 1.1 million g/mol.

The cationic copolymer can include an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer can include a cationic monomer selected from the group consisting of: trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters can be cationized esters of the (meth)acrylic acid containing a quaternized N atom. Cationized esters of the (meth)acrylic acid containing a quaternized N atom can be quaternized dialkylaminoalkyl (meth)acrylates with $C_1$ to $C_3$ in the alkyl and alkylene groups. The cationized esters of the (meth)acrylic acid containing a quaternized N atom can be selected from the group consisting of ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth)acrylate; and diethylaminopropyl (meth)acrylate quaternized with methyl chloride. The cationized esters of the (meth)acrylic acid containing a quaternized N atom can be dimethylaminoethyl acrylate, which is quaternized with an alkyl halide, or with methyl chloride or benzyl chloride or dimethyl sulfate (ADAME-Quat). The cationic monomer when based on (meth)acrylamides are quaternized dialkylaminoalkyl(meth)acrylamides with $C_1$ to $C_3$ in the alkyl and alkylene groups, or dimethylaminopropylacrylamide, which is quaternized with an alkyl halide, or methyl chloride or benzyl chloride or dimethyl sulfate.

The cationic monomer based on a (meth)acrylamide can be a quaternized dialkylaminoalkyl(meth)acrylamide with $C_1$ to $C_3$ in the alkyl and alkylene groups. The cationic monomer based on a (meth)acrylamide can be dimethylaminopropylacrylamide, which is quaternized with an alkyl halide, especially methyl chloride or benzyl chloride or dimethyl sulfate.

The cationic monomer can be a hydrolysis-stable cationic monomer. Hydrolysis-stable cationic monomers can be, in addition to a dialkylaminoalkyl(meth)acrylamide, any monomer that can be regarded as stable to the OECD hydrolysis test. The cationic monomer can be hydrolysis-stable and the hydrolysis-stable cationic monomer can be selected from the group consisting of: diallyldimethylammonium chloride and water-soluble, cationic styrene derivatives.

The cationic copolymer can be a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer can be formed from acrylamide and acrylamidopropyltrimethylammonium chloride, wherein the acrylamidopropyltrimethylammonium chloride has a charge density of 1.0 meq/g to 3.0 meq/g.

The cationic copolymer can have a charge density of 1.1 meq/g to 2.5 meq/g, 1.1 meq/g to 2.3 meq/g, 1.2 meq/g to 2.2 meq/g, 1.2 meq/g to 2.1 meq/g, 1.3 meq/g to 2.0 meq/g, and 1.3 meq/g to 1.9 meq/g.

The cationic copolymer can have a M.Wt. 100 thousand g/mol to 2 million g/mol, 300 thousand g/mol to 1.8 million g/mol, 500 thousand g/mol to 1.6 million g/mol, 700 thousand g/mol to 1.4 million g/mol, and 900 thousand g/mol to 1.2 million g/mol.

The cationic copolymer can be a trimethylammoniopropylmethacrylamide chloride-N-Acrylamide copolymer, which is also known as AM:MAPTAC and can have a charge density of 1.3 meq/g and a M.Wt. of 1.1 million g/mol. The cationic copolymer can be AM:ATPAC and can have a charge density of 1.8 meq/g and a M.Wt. of 1.1 million g/mol.

Synthetic Polymers

A cationic polymer can be a synthetic polymer that is formed from:
i) one or more cationic monomer units, and optionally
ii) one or more monomer units bearing a negative charge, and/or
iii) a nonionic monomer,
wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers The cationic polymers can be water soluble or dispersible, non-crosslinked, and synthetic cationic polymers which have the structure of Formula XIII:

(XIII)

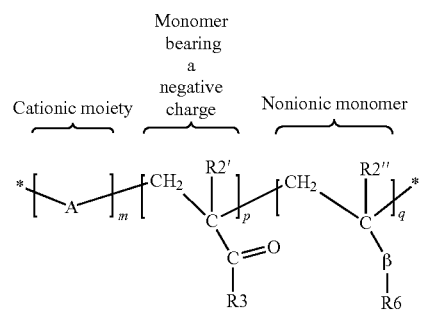

$m \geq 1$
$p = 0$ or $\geq 1$
$q = 0$ or $\geq 1$
$m \geq p$ where A may be one or more of the following cationic moieties:

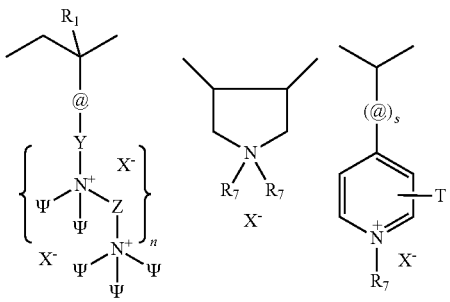

where @=amido, alkylamido, ester, ether, alkyl or alkylaryl,
where Y=C1-C22 alkyl, alkoxy, alkylidene, alkyl or aryloxy,
where ψ=C1-C22 alkyl, alkyloxy, alkyl aryl or alkyl arylox,
where Z=C1-C22 alkyl, alkyloxy, aryl or aryloxy,
where $R_1$=H, C1-C4 linear or branched alkyl,
where s=0 or 1, n=0 or ≥1,
where T and $R_7$=C1-C22 alkyl,
where X-=halogen, hydroxide, alkoxide, sulfate or alkylsulfate;
where the monomer bearing a negative charge is defined by R2'=H, $C_1$-$C_4$ linear or branched alkyl and R3 is:

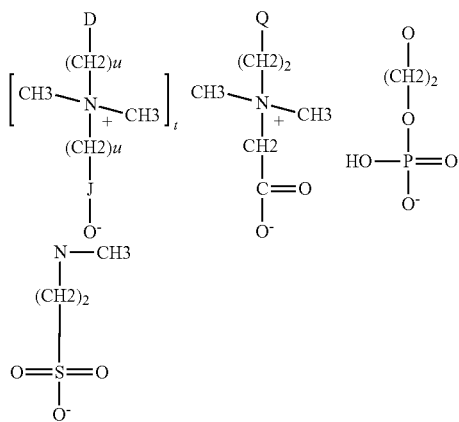

where D=O, N, or S;
where Q=$NH_2$ or O;
where u=1-6;
where t=0-1; and
where J=oxygenated functional group containing the following elements P, S, C; and
where the nonionic monomer is defined by R2″=H, $C_1$-$C_4$ linear or branched alkyl, R6=linear or branched alkyl, alkyl aryl, aryl oxy, alkyloxy, alkylaryl oxy and β is defined as:

where G' and G″ are, independently of one another, O, S or N—H and L=0 or 1.

Suitable monomers can include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of suitable cationic monomers can include dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers can include quaternary monomers of formula —$NR_3^+$, wherein each R can be identical or different, and can be a hydrogen atom, an alkyl group comprising 1 to 10 carbon atoms, or a benzyl group, optionally carrying a hydroxyl group, and including an anion (counter-ion). Examples of suitable anions include halides such as chlorides, bromides, sulphates, hydrosulphates, alkylsulphates (for example comprising 1 to 6 carbon atoms), phosphates, citrates, formates, and acetates.

Suitable cationic monomers can also include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride. Additional suitable cationic monomers can include trimethyl ammonium propyl (meth)acrylamido chloride. Examples of monomers bearing a negative charge include alpha ethylenically unsaturated monomers including a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge can include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers can include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth)acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers can also include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion ($X^-$) in association with the synthetic cationic polymers can be any known counterion so long as the polymers remain soluble or dispersible in water, in the shampoo composition, or in a coacervate phase of the shampoo composition, and so long as the counterions are physically and chemically compatible with the essential components of the shampoo composition or do not otherwise unduly impair product performance, stability or aesthetics. Non limiting examples of suitable counterions can include halides (e.g., chlorine, fluorine, bromine, iodine), sulfate, and methylsulfate.

The cationic polymer described herein can also aid in repairing damaged hair, particularly chemically treated hair by providing a surrogate hydrophobic F-layer. The microscopically thin F-layer provides natural weatherproofing, while helping to seal in moisture and prevent further damage. Chemical treatments damage the hair cuticle and strip away its protective F-layer. As the F-layer is stripped away, the hair becomes increasingly hydrophilic. It has been found that when lyotropic liquid crystals are applied to chemically treated hair, the hair becomes more hydrophobic and more virgin-like, in both look and feel. Without being limited to any theory, it is believed that the lyotropic liquid crystal complex creates a hydrophobic layer or film, which coats the hair fibers and protects the hair, much like the natural F-layer protects the hair. The hydrophobic layer can return the hair to a generally virgin-like, healthier state. Lyotropic liquid crystals are formed by combining the synthetic cationic polymers described herein with the aforementioned anionic detersive surfactant component of the shampoo composition. The synthetic cationic polymer has a relatively high charge density. It should be noted that some synthetic polymers having a relatively high cationic charge density do not form lyotropic liquid crystals, primarily due to their abnormal linear charge densities. Such synthetic cationic polymers are described in PCT Patent App. No. WO 94/06403 which is incorporated by reference. The synthetic polymers described herein can be formulated in a stable shampoo composition that provides improved conditioning performance, with respect to damaged hair.

Cationic synthetic polymers that can form lyotropic liquid crystals have a cationic charge density of 2 meq/gm to 7 meq/gm, and/or 3 meq/gm to 7 meq/gm, and/or 4 meq/gm to 7 meq/gm. The cationic charge density is 6.2 meq/gm. The polymers also have a M. Wt. of 1,000 to 5,000,000, and/or 10,000 to 2,000,000, and/or 100,000 to 2,000,000.

Cationic synthetic polymers that provide enhanced conditioning and deposition of benefit agents but do not necessarily form lytropic liquid crystals can have a cationic charge density of 0.7 meq/gm to 7 meq/gm, and/or 0.8 meq/gm to 5 meq/gm, and/or 1.0 meq/gm to 3 meq/gm. The polymers also have a M.Wt. of 1,000 g/mol to 5,000,000 g/mol, 10,000 g/mol to 2,000,000 g/mol, and 100,000 g/mol to 2,000,000 g/mol.

Cationic Cellulose Polymer

Suitable cationic polymers can be cellulose polymers. Suitable cellulose polymers can include salts of hydroxyethyl cellulose reacted with trimethyl ammonium substituted epoxide, referred to in the industry (CTFA) as Polyquaternium 10 and available from Dwo/Amerchol Corp. (Edison, N.J., USA) in their Polymer LR, JR, and KG series of polymers. Other suitable types of cationic cellulose can include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose can include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

Additional cationic polymers are also described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)), which is incorporated herein by reference.

Techniques for analysis of formation of complex coacervates are known in the art. For example, microscopic analyses of the compositions, at any chosen stage of dilution, can be utilized to identify whether a coacervate phase has formed. Such coacervate phase can be identifiable as an additional emulsified phase in the composition. The use of dyes can aid in distinguishing the coacervate phase from other insoluble phases dispersed in the composition. Additional details the use of cationic polymers and coacervates are disclosed in U.S. Pat. No. 9,272,164 which is incorporated by reference.

Liquid Carrier for the Shampoo Composition

The shampoo composition also includes a liquid carrier. Inclusion of an appropriate quantity of a liquid carrier can facilitate the formation of a shampoo composition having an appropriate viscosity and rheology. A shampoo composition can include, by weight of the composition, 60% to 95% of a liquid carrier, 65% to 92%, 70% to 90% of a liquid carrier, and 75% to 90% of a liquid carrier.

A liquid carrier can be water or a miscible mixture of water and organic solvent. A liquid carrier can be water with minimal or no significant concentrations of organic solvent, except as otherwise incidentally incorporated into the composition as minor ingredients of other essential or optional components. Suitable organic solvents can include water solutions of lower alkyl alcohols and polyhydric alcohols. Useful lower alkyl alcohols include monohydric alcohols having 1 to 6 carbons, such as ethanol and isopropanol. Exemplary polyhydric alcohols include propylene glycol, hexylene glycol, glycerin, and propane diol.

Optional Components

As can be appreciated, shampoo compositions described herein can include a variety of optional components to tailor the properties and characteristics of the composition. As can be appreciated, suitable optional components are well known and can generally include any components which are physically and chemically compatible with the essential components of the shampoo compositions described herein. Optional components should not otherwise unduly impair product stability, aesthetics, or performance Individual concentrations of optional components can generally range 0.001% to 10%, by weight of a shampoo composition.

Suitable optional components which can be included in a shampoo composition can include natural ingredients such as, tea extracts, and natural antioxidants such as grape seed extracts, natural hair conditioning oils, such as safflower oil, jojoba oil, argon oil, and combinations thereof.

Suitable optional components which can be included in a shampoo composition can include, deposition aids, conditioning agents (including hydrocarbon oils, fatty esters, silicones), anti-dandruff agents, suspending agents, viscosity modifiers, dyes, nonvolatile solvents or diluents (water soluble and insoluble), pearlescent aids, foam boosters, pediculocides, pH adjusting agents, perfumes, preservatives, chelants, proteins, skin active agents, sunscreens, UV absorbers, and vitamins.

Silicone Emulsions

The hair care composition can comprise 0% to 10%, 0.1% to 8%, 0.1% to 5%, 0.1% to 4%, 0.1% to 3%, 0.1% to 2%, 0.1% to 1.5%, and/or 0.1% to 1.2%, by weight, of one of more silicone polymers. The silicone polymer can be added into the hair care composition as an aqueous pre-emulsion. The silicone pre-emulsion can comprise one or more silicone polymers and an emulsifying system. The silicone polymer content in the silicone pre-emulsion can be 10%, by weight, to 70%, by weight, or 15%, by weight, to 60%, by weight, or 18%, by weight, to 50% by weight.

The silicone emulsion can have an average particle size of less than 500 nm, alternatively 300 nm, alternatively less than 200 nm, and alternatively less than 100 nm. The silicone emulsion can have an average particle size of 5 nm to 500 nm, 10 nm to 400 nm, and/or 20 nm to 300 nm. The silicone emulsion can be in the form of a nano-emulsion.

The particle size of the one or more silicones may be measured by dynamic light scattering (DLS). A Malvern Zetasizer Nano ZEN3600 system using He—Ne laser 633 nm may be used for the measurement at 25° C.

The autocorrelation function may be analyzed using the Zetasizer Software provided by Malvern Instruments, which determines the effective hydrodynamic radius, using the Stokes-Einstein equation:

$$D = \frac{k_B T}{6\pi\eta R}$$

wherein $k_B$ is the Boltzmann Constant, T is the absolute temperature, $\eta$ is the viscosity of the medium, D is the mean diffusion coefficient of the scattering species, and R is the hydrodynamic radius of particles.

Particle size (i.e. hydrodynamic radius) may be obtained by correlating the observed speckle pattern that arises due to Brownian motion and solving the Stokes-Einstein equation, which relates the particle size to the measured diffusion constant, as is known in the art.

For each sample, 3 measurements may be made and Z-average values may be reported as the particle size.

The one or more silicones may be in the form of a nanoemulsion. The nanoemulsion may comprise any silicone suitable for application to the skin and/or hair.

The one or more silicones may include in their molecular structure polar functional groups such as Si—OH (present in dimethiconols), primary amines, secondary amines, tertiary amines, and quaternary ammonium salts. The one or more silicones may be selected from aminosilicones, pendant quaternary ammonium silicones, terminal quaternary ammonium silicones, amino polyalkylene oxide silicones, quaternary ammonium polyalkylene oxide silicones, and amino morpholino silicones.

The one or more silicones may comprise:
(a) at least one aminosilicone corresponding to formula (XIV):

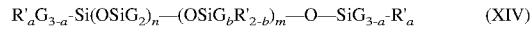

R'$_a$G$_{3-a}$-Si(OSiG$_2$)$_n$-(OSiG$_b$R'$_{2-b}$)$_m$-O-SiG$_{3-a}$-R'$_a$      (XIV)

where:
G is chosen from a hydrogen atom, a phenyl group, OH group, and C$_1$-C$_8$ alkyl groups, for example methyl,
a is an integer ranging from 0 to 3, and in one embodiment a is 0,
b is chosen from 0 and 1, and in one embodiment b is 1,
m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10;
R' is a monovalent group of formula —C$_q$H$_{2q}$L in which q is a number from 2 to 8 and L is an optionally quaternized amine group chosen from the groups:

—NR"—CH$_2$—CH$_2$—N'(R$^1$)$_2$,

—N(R")$_2$,

—N$^+$(R")$_3$A$^-$,

—N$^+$H(R")$_2$A$^-$,

—N$^+$$_2$(R")A$^-$, and

—N(R")—CH$_2$—CH$_2$—N$^+$R"H$_2$A$^-$,

Where R" can be chosen from a hydrogen atom, phenyl groups, benzyl groups, and saturated monovalent hydrocarbon-based groups such as, for example, an alkyl group comprising from 1 to 20 carbon atoms, and A$^-$ is chosen from halide ions such as, for example, fluoride, chloride, bromide and iodide.

The one or more silicones may include those corresponding to formula (XIV) wherein a=0, G=methyl, m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10; and L is —N(CH$_3$)$_2$ or —NH$_2$, alternatively —NH$_2$.

Additional said at least one aminosilicone of the invention include:
(b) pendant quaternary ammonium silicones of formula (XV):

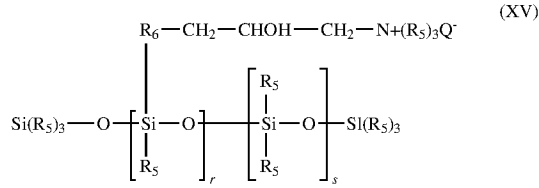

where:
$R_5$ is chosen from monovalent hydrocarbon-based groups comprising from 1 to 18 carbon atoms, such as $C_1$-$C_{18}$ alkyl groups and $C_2$-$C_{18}$ alkenyl groups, for example methyl;
$R_6$ is chosen from divalent hydrocarbon-based groups, such as divalent $C_1$-$C_{18}$ alkylene groups and divalent $C_1$-$C_{18}$ alkylenoxy groups, for example $C_1$-$C_8$ alkylenoxy groups, wherein said $R_6$ is bonded to the Si by way of an SiC bond;
$Q^-$ is an anion that can be for example chosen from halide ions, such as chloride, and organic acid salts (such as acetate);
r is an average statistical value ranging from 2 to 20, such as from 2 to 8;
s is an average statistical value ranging from 20 to 200, such as from 20 to 50.

Such aminosilicones are described more particularly in U.S. Pat. No. 4,185,087, the disclosure of which is incorporated by reference herein.

A silicone which falls within this class is the silicone sold by the company Union Carbide under the name "Ucar Silicone ALE 56".

Further examples of said at least one aminosilicone include:
c) quaternary ammonium silicones of formula (XVI):

(XVI)

$$R_8 - \overset{R_7}{\underset{R_7}{N^+}} - CH_2 - \overset{OH}{\underset{}{CH}} - CH_2 - R_6 \left[ \overset{R_7}{\underset{R_7}{Si}} - O \right]_r \overset{R_7}{\underset{R_7}{Si}} - R_6 - CH_2 - CHOH - CH_2 - \overset{R_7}{\underset{R_7}{N^+}} - R_8 \quad 2X''$$

where:
groups $R_7$, which may be identical or different, are each chosen from monovalent hydrocarbon-based groups comprising from 1 to 18 carbon atoms, such as $C_1$-$C_{18}$ alkyl groups, for example methyl, $C_2$-$C_{18}$ alkenyl groups, and rings comprising 5 or 6 carbon atoms;
R6 is chosen from divalent hydrocarbon-based groups, such as divalent $C_1$-$C_{18}$ alkylene groups and divalent $C_1$-$C_{18}$alkylenoxy, for example $C_1$-$C_8$, group connected to the Si by an SiC bond;
$R_8$, which may be identical or different, represent a hydrogen atom, a monovalent hydrocarbon-based group comprising from 1 to 18 carbon atoms, and in particular a $C_1$-$C_{18}$ alkyl group, a $C_2$-$C_{18}$ alkenyl group or a group —$R_6$—NHCOR$_7$;
$X^-$ is an anion such as a halide ion, in particular chloride, or an organic acid salt (acetate, etc.);
r represents an average statistical value from 2 to 200 and in particular from 5 to 100.

Such silicones are described, for example, in application EP-A-0 530 974, the disclosure of which is incorporated by reference herein.
Silicones falling within this class are the silicones sold by the company Eovnik under the names Abil Quat 3270, Abil Quat 3272, Abil Quat 3474 and Abil ME 45.

Further examples of said at least one aminosilicone include:
d) quaternary ammonium and polyalkylene oxide silicones wherein the quaternary nitrogen groups are located in the polysiloxane backbone, at the termini, or both.
Such silicones are described in PCT Publication No. WO 2002/010257, the disclosure of which is incorporated by reference herein.
Silicones falling within this class are the silicones sold by the company Momentive under the names Silsoft Q.

(e) Aminofunctional silicones having morpholino groups of formula (XVII):

(XVII)

$$B + \underset{CH_3}{\overset{CH_3}{Si}} - O \underset{a}{]} + \underset{}{\overset{A}{Si}} - O \underset{a}{]} + \underset{CH_3}{\overset{CH_3}{Si}} - O \underset{b}{]} + \underset{CH_3}{\overset{CH_3}{Si}} - O \underset{n}{]} + \underset{CH_3}{\overset{CH_3}{Si}} - O \underset{n}{]} - D,$$

where A denotes a structural unit (a), (b), or (c) bound via —O—

(a)

$$* - \underset{CH_3}{\overset{CH_3}{Si}} - O \underset{m}{]} - *$$
$\quad\quad Cl^-$ (b)

$$* - \underset{}{\overset{CH_3}{Si}} - O \underset{n}{]} - *$$
$\quad\quad Cl^-$ (c)

$$* - \underset{}{\overset{A}{Si}} - O \underset{o}{]} - *,$$

or an oligomeric or polymeric residue, bound via —O—, containing structural units of formulas (I), (II), or (III), or half of a connecting oxygen atom to a structural unit (III), or denotes —OH,

* denotes a bond to one of the structural units (I), (II), or (III), or denotes a terminal group B (Si-bound) or D (O-bound), B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers between 0 and 1000, with the provision that a+b+c>0, m, n, and o denote integers between 1 and 1000.

Aminofunctional silicones of this kind bear the INCI name: Amodimethicone/Morpholinomethyl Silsesquioxane Copolymer. A particularly suitable amodimethicone is the product having the commercial name Wacker Belsil® ADM 8301E.

Examples of such silicones are available from the following suppliers:
offered by the company Dow Corning: Fluids: 2-8566, AP 6087, AP 6088, DC 8040 Fluid, fluid 8822A DC, DC 8803 & 8813 polymer, 7-6030, AP-8104, AP 8201; Emulsions: CE-8170 AF Micro Emulsion, 2-8177, 2-8194 Microemulsion, 9224 Emulsion, DC 1872 Emulsion, 939, 949, 959, DC 5-7113 Quat Microemulsion, DC 5-7070 Emulsion, DC CE-8810, CE 8401 Emulsion, CE 1619, Dow Corning Toray SS-3551, Dow Corning Toray SS-3552;

offered by the company Wacker: Wacker Belsil ADM 652, ADM 656, 1100, 1600, 1650 (fluids) ADM 6060 (linear amodimethicone) emulsion; ADM 6057 E (branched amodimethicone) emulsion; ADM 8020 VP (micro emulsion); SLM 28040 (micro emulsion); DM5500 emulsion;

offered by the Company Momentive: Silsoft 331, SF1708, SME 253 & 254 (emulsion), SM2125 (emulsion), SM 2658 (emulsion), Silsoft Q (emulsion)

offered by the company Shin-Etsu: KF-889, KF-867S, KF-8004, X-52-2265 (emulsion);

offered by the Company Siltech Silicones: Siltech E-2145, E-Siltech 2145-35;

offered by the company Evonik Industries: Abil T Quat 60th

Some non-limiting examples of aminosilicones include the compounds having the following INCI names Silicone Quaternium-1, Silicone Quaternium-2, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-17, Silicone Quaternium-18, Silicone Quaternium-20, Silicone Quaternium-21, Silicone Quaternium-22, Quaternium-80, as well as Silicone Quaternium-2 Panthenol Succinate and Silicone Quaternium-16/Glycidyl Dimethicone Crosspolymer.

The aminosilicones can be supplied in the form of a nanoemulsion and include MEM 9049, MEM 8177, MEM 0959, MEM 8194, SME 253, and Silsoft Q.

The one or more silicones may include dimethicones, and/or dimethiconols. The dimethiconols are hydroxyl terminated dimethylsilicones represented by the general chemical formulas

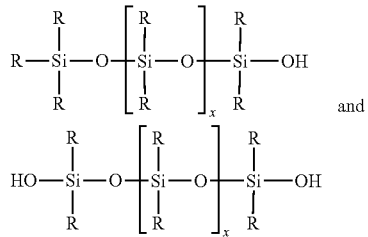

where R is an alkyl group (preferably R is methyl or ethyl, more preferably methyl) and x is an integer up to 500, chosen to achieve the desired molecular weight. Commercial dimethiconols typically are sold as mixtures with dimethicone or cyclomethicone (e.g., Dow Corning® 1401, 1402, and 1403 fluids).

According to another aspect of the silicone emulsion, the emulsion further includes an anionic surfactant that participates in providing high internal phase viscosity emulsions having particle sizes in the range 30 nm to 10 micron. The anionic surfactant is selected from organic sulfonic acids. Most common sulfonic acids used in the present process are alkylaryl sulfonic acid; alkylaryl polyoxyethylene sulphonic acid; alkyl sulfonic acid; and alkyl polyoxyethylene sulfonic acid. General formulas of the sulfonic acids are as shown below:

R16C6H4SO3H,
R16C6H4O(C2H4O)mSO3H,
R16SO3H, and
R16O(C2H4O)mSO3H.

Where R16, which may differ, is a monovalent hydrocarbon radical having at least 6 carbon atoms. Non-limiting examples of R16 include hexyl, octyl, decyl, dodecyl, cetyl, stearyl, myristyl, and oleyl. 'm' is an integer from 1 to 25. Exemplary anionic surfactants include but are not limited to octylbenzene sulfonic acid; dodecylbenzene sulfonic acid; cetylbenzene sulfonic acid; alpha-octyl sulfonic acid; alpha-dodecyl sulfonic acid; alpha-cetyl sulfonic acid; polyoxyethylene octylbenzene sulfonic acid; polyoxyethylene dodecylbenzene sulfonic acid; polyoxyethylene cetylbenzene sulfonic acid; polyoxyethylene octyl sulfonic acid; polyoxyethylene dodecyl sulfonic acid; and polyoxyethylene cetyl sulfonic acid. Generally, 1 to 15% anionic surfactant is used in the emulsion process. For example, 3-10% anionic surfactant can be used to obtain an optimum result. The silicone emulsion may further include an additional emulsifier together with the anionic surfactant, which along with the controlled temperature of emulsification and polymerization, facilitates making the emulsion in a simple and faster way. Non-ionic emulsifiers having a hydrophilic lipophilic balance (HLB) value of 10 to 19 are suitable and include polyoxyalkylene alkyl ether, polyoxyalkylene alkylphenyl ethers and polyoxyalkylene sorbitan esters. Some useful emulsifiers having an HLB value of 10 to 19 include, but are not limited to, polyethylene glycol octyl ether; polyethylene glycol lauryl ether; polyethylene glycol tridecyl ether; polyethylene glycol cetyl ether; polyethylene glycol stearyl ether; polyethylene glycol nonylphenyl ether; polyethylene glycol dodecylphenyl ether; polyethylene glycol cetylphenyl ether; polyethylene glycol stearylphenyl ether; polyethylene glycol sorbitan mono stearate; and polyethylene glycol sorbitan mono oleate.

Non-Silicone Conditioning Agents

The conditioning agent of the hair care compositions described herein may also comprise at least one organic conditioning agents, either alone or in combination with other conditioning agents, such as the silicones described above. Non-limiting examples of organic conditioning agents are described below.

a. Hydrocarbon Oils

Suitable organic conditioning agents for use as conditioning agents in hair care compositions include, but are not limited to, hydrocarbon oils having at least 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils can be $C_{12}$ to $C_{19}$. Branched chain hydrocarbon oils, including hydrocarbon polymers, typically will contain more than 19 carbon atoms.

b. Polyolefins

Organic conditioning oils for use in the hair care compositions described herein also include liquid polyolefins, including liquid poly-α-olefins and/or hydrogenated liquid poly-α-olefins. Polyolefins for use herein are prepared by polymerization of $C_4$ to $C_{14}$ olefinic monomers, alternatively $C_6$ to $C_{12}$.

c. Fatty Esters

Other suitable organic conditioning agents for use as a conditioning agent in the hair care compositions described herein include fatty esters having at least 10 carbon atoms.

These fatty esters include esters with hydrocarbyl chains derived from fatty acids or alcohols. The hydrocarbyl radicals of the fatty esters hereof may include or have covalently bonded thereto other compatible functionalities, such as amides and alkoxy moieties (e.g., ethoxy or ether linkages, etc.). Other oligomeric or polymeric esters, prepared from unsaturated glyceryl esters can also be used as conditioning materials.

d. Fluorinated Conditioning Compounds

Fluorinated compounds suitable for delivering conditioning to hair as organic conditioning agents include perfluoropolyethers, perfluorinated olefins, fluorine-based specialty polymers that may be in a fluid or elastomer form similar to the silicone fluids previously described, and perfluorinated dimethicones.

e. Fatty Alcohols

Other suitable organic conditioning oils for use in the hair care compositions described herein include, but are not limited to, fatty alcohols having at least 10 carbon atoms, 10 to 22 carbon atoms, and alternatively 12 to 16 carbon atoms.

f. Alkyl Glucosides and Alkyl Glucoside Derivatives

Suitable organic conditioning oils for use in the hair care compositions described herein include, but are not limited to, alkyl glucosides and alkyl glucoside derivatives. Specific non-limiting examples of suitable alkyl glucosides and alkyl glucoside derivatives include Glucam E-10, Glucam E-20, Glucam P-10, and Glucquat 125 commercially available from Amerchol.

g. Polyethylene Glycols

Additional compounds useful herein as conditioning agents include polyethylene glycols and polypropylene glycols having a molecular weight of up to 2,000,000 such as those with CTFA names PEG-200, PEG-400, PEG-600, PEG-1000, PEG-2M, PEG-7M, PEG-14M, PEG-45M and mixtures thereof.

2. Emulsifiers

A variety of anionic and nonionic emulsifiers can be used in the hair care compositions. The anionic and nonionic emulsifiers can be either monomeric or polymeric in nature. Monomeric examples include, by way of illustrating and not limitation, alkyl ethoxylates, alkyl sulfates, soaps, and fatty esters and their derivatives. Polymeric examples include, by way of illustrating and not limitation, polyacrylates, polyethylene glycols, and block copolymers and their derivatives. Naturally occurring emulsifiers such as lanolins, lecithin and lignin and their derivatives are also non-limiting examples of useful emulsifiers.

Anti-Dandruff Actives

A shampoo composition can also contain an anti-dandruff agent. Suitable anti-dandruff agents can include pyridinethione salts, azoles, selenium sulfide, particulate sulfur, and mixtures thereof. Such anti-dandruff particulate should be physically and chemically compatible with the essential components of the composition, and should not otherwise unduly impair product stability, aesthetics or performance A shampoo composition can include a cationic polymer to enhance deposition of an anti-dandruff active.

a. Pyridinethione Salts

An anti-dandruff agent can be a pyridinethione particulate such as a 1-hydroxy-2-pyridinethione salt. The concentration of pyridinethione anti-dandruff particulates can range 0.1% to 4%, 0.1% to 3%, and 0.3% to 2% by weight of the composition. Suitable pyridinethione salts include those formed from heavy metals such as zinc, tin, cadmium, magnesium, aluminum and zirconium, particularly suitable is the zinc salt of 1-hydroxy-2-pyridinethione (known as "zinc pyridinethione" or "ZPT"), 1-hydroxy-2-pyridinethione salts in platelet particle form, wherein the particles have an average size of up to 20μ, up to 5μ, up to 2.5 Salts formed from other cations, such as sodium, can also be suitable. Pyridinethione anti-dandruff agents are further described in U.S. Pat. Nos. 2,809,971; 3,236,733; 3,753,196; 3,761,418; 4,345,080; 4,323,683; 4,379,753; and 4,470,982, each of which are incorporated herein by reference. It is contemplated that when ZPT is used as the anti-dandruff particulate, that the growth or re-growth of hair may be stimulated or regulated, or both, or that hair loss may be reduced or inhibited, or that hair may appear thicker or fuller.

b. Other Anti-Microbial Actives

In addition to the anti-dandruff active selected from polyvalent metal salts of pyrithione, a shampoo composition can further include one or more anti-fungal or anti-microbial actives in addition to the metal pyrithione salt actives. Suitable anti-microbial actives include coal tar, sulfur, whitfield's ointment, castellani's paint, aluminum chloride, gentian violet, octopirox (piroctone olamine), ciclopirox olamine, undecylenic acid and it's metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Suitable anti-microbials can include itraconazole, ketoconazole, selenium sulphide and coal tar.

c. Soluble Anti-Dandruff Agent

A suitable anti-microbial agent can be one material or a mixture selected from: azoles, such as climbazole, ketoconazole, itraconazole, econazole, and elubiol; hydroxy pyriclones, such as piroctone olamine, ciclopirox, rilopirox, and MEA-Hydroxyoctyloxypyridinone; kerolytic agents, such as salicylic acid and other hydroxy acids; strobilurins such as azoxystrobin and metal chelators such as 1,10-phenanthroline. Examples of azole anti-microbials can include imidazoles such as benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in a shampoo composition, the soluble anti-microbial active can be included in an amount 0.01% to 5%, 0.5% to 6%, 0.1% to 3%, 0.1% to 9%, OA % to 1.5%, OA % to 2%, and more 0.3% to 2%, by weight of the composition.

d. Selenium Sulfide

Selenium sulfide is a particulate anti-dandruff agent suitable for use as an anti-microbial compositions when included at concentrations of 0.1% to 4%, by weight of the composition, 0.3% to 2.5% by weight, and 0.5% to 1.5% by weight. Selenium sulfide is generally regarded as a compound having one mole of selenium and two moles of sulfur, although it may also be a cyclic structure that conforms to the general formula $Se_xS_y$, wherein x+y=8. Average particle diameters for the selenium sulfide are typically less than 15 μm, as measured by forward laser light scattering device (e.g. Malvern 3600 instrument), less than 10 pm. Selenium sulfide compounds are described, for example, in U.S. Pat. Nos. 2,694,668; 3,152,046; 4,089,945; and 4,885,107, each of which are incorporated herein by reference.

e. Sulfur

Sulfur can also be used as a particulate anti-microbial/anti-dandruff agent. Effective concentrations of the particulate sulfur are typically 1% to 4%, by weight of the composition, alternatively 2% to 4%.

f. Keratolytic Agents

Keratolytic agents such as salicylic acid can also be included in a shampoo composition described herein.

g. Other

Additional anti-microbial actives can include extracts of melaleuca (tea tree), wintergreen (such as gaultheria procumbens leaf) and charcoal. As can be appreciated, shampoo compositions can also include combinations of anti-microbial actives. Suitable combinations can include octopirox and zinc pyrithione combinations, pine tar and sulfur combinations, salicylic acid and zinc pyrithione combinations, octopirox and climbasole combinations, and salicylic acid and octopirox combinations, and mixtures thereof.

Humectant

A shampoo composition can also include a humectant to lower the rate of water evaporation. Suitable humectants can include polyhydric alcohols, water soluble alkoxylated nonionic polymers, and mixtures thereof. The humectants, when included, can be used at levels by weight of the composition of 0.1% to 20%, and 0.5% to 5%.

Suitable polyhydric alcohols can include glycerin, sorbitol, propylene glycol, butylene glycol, hexylene glycol, ethoxylated glucose, 1, 2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof.

Suitable water soluble alkoxylated nonionic polymers can include polyethylene glycols and polypropylene glycols having a molecular weight of up to 1000 such as those with CTFA names PEG-200, PEG-400, PEG-600, PEG-1000, and mixtures thereof.

Other Optional Components

As can be appreciated, a shampoo composition can include still further optional components. For example, amino acids can be included. Suitable amino acids can include water soluble vitamins such as vitamins B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their derivatives, water insoluble amino acids such as tyrosine, tryptamine, and their salts.

A shampoo composition can include pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C. I. Names. The compositions can also include antimicrobial agents which are useful as cosmetic biocides and antidandruff agents including: water soluble components such as piroctone olamine, water insoluble components such as 3,4,4'-trichlorocarbanilide (trichlosan), triclocarban and zinc pyrithione.

One or more stabilizers and preservatives can be included. For example, one or more of trihydroxystearin, ethylene glycol distearate, citric acid, sodium citrate dihydrate, a preservative such as kathon, sodium chloride, sodium benzoate, and ethylenediaminetetraacetic acid ("EDTA") can be included to improve the lifespan of a shampoo composition.

Chelants can also be included to scavenge metal and reduce hair damage caused by exposure to UV radiation. Examples of suitable chelants can include histidine and N,N' ethylenediamine disuccinic acid ("EDDS").

Method of Use

The shampoo compositions described herein can be used in a conventional manner for cleansing and conditioning of hair or skin. Generally, a method of treating hair or skin can include applying the shampoo composition to the hair or skin. For example, an effective amount of the shampoo composition can be applied to the hair or skin, which has been wetted with water, and then the composition can be rinsed off. Effective amounts can generally range 1 g to 50 g, and 1 g to 20 g. Application to the hair typically includes working the composition through the hair such that most or all of the hair is contacted with the composition.

A method for treating the hair or skin can include the steps of: (a) wetting the hair or skin with water; (b) applying an effective amount of the shampoo composition to the hair or skin, and (c) rinsing the applied areas of skin or hair with water. These steps can be repeated as many times as desired to achieve the desired cleansing and conditioning benefit.

A shampoo composition as described herein can be used to treat damaged hair. Damaged hair can include hair permed hair, oxidatively colored hair, and mechanically damaged hair.

The shampoo compositions can be used as liquids, solids, semi-solids, flakes, gels, in a pressurized container with a propellant added, or used in a pump spray form. The viscosity of the product may be selected to accommodate the form desired.

TEST METHODS

A. Cone/Plate Viscosity Measurement

The viscosities of the examples are measured by a Cone/Plate Controlled. Stress Brookfield Rheometer R/S Plus, by Brookfield Engineering Laboratories, Stoughton, Mass. The cone used (Spindle C-75-1) has a diameter of 75 mm and 1° angle. The viscosity is determined using a steady state flow experiment at constant shear rate of 2 and at temperature of 26.5° C. The sample size is 2.5 nil and the total measurement reading time is 3 minutes.

B. pH Method

First, calibrate the Mettler Toledo Seven Compact pH meter. Do this by turning on the pH meter and waiting for 30 seconds. Then take the electrode out of the storage solution, rinse the electrode with distilled water, and carefully wipe the electrode with a scientific cleaning wipe, such as a Kimwipe®. Submerse the electrode in the pH 4 buffer and press the calibrate button. Wait until the icon stops flashing and press the calibrate button a second time. Rinse the electrode with distilled water and carefully wipe the electrode with a scientific cleaning wipe. Then submerse the electrode into the pH 7 buffer and press the calibrate button a second time. Wait until the pH icon stops flashing and press the calibrate button a third time. Rinse the electrode with distilled water and carefully wipe the electrode with a scientific cleaning wipe. Then submerse the electrode into the pH 10 buffer and press the calibrate button a third time. Wait until the pH icon stops flashing and press the measure button. Rinse the electrode with distilled water and carefully wipe with a scientific cleaning wipe.

Submerse the electrode into the testing sample and press the read button. Wait until the pH icon stops flashing and record the value.

C. Appearance Method

Following batch completion, first transfer batch to storage container. Second, sample batch in a glass vial. Third, visually inspect the sample. If the background can be seen distinctly record the appearance as transparent. If the background can be seen but distorted or hazy, record as semi-transparent. If the background cannot be seen record as opaque.

D. Phase Stability Method

Following batch completion, first transfer batch to storage container. Second, sample batch in a glass vial. Third, visually inspect the sample. If sample is homogeneous record as one phase. If sample has two or more distinct phases record as phase separated including number of phases present. Distinct phases are visually different (changes in hazy, color, texture). These distinct phases either settle to the bottom, on top or are suspended.

E. Hair Switch Evaluation

This method describes how to evaluate finished product on hair switches. First, wet hair for 15 seconds. Second, apply shampoo to hair switch; 0.1 g of shampoo per gram of hair. Then assess different attributes of shampoo performance on the hair throughout wash. Move hands up and down hair switch for 30 seconds. During these 30 seconds the following are assessed.

1.) Speed to Lather—Assessment of how quickly lather is generated (Scale: 0=Slow to 10=Fast)
2.) Lather Amount—Visual assessment of how much lather is generated (Scale: 0=Low to 10=High)

Next, run water over switch to begin rinsing. Rinse for 30 seconds. During the rinse assess the Rinse Feel/Rinse Count Drag. As soon as wetting begins, stroke the hair from top to bottom with non-dominant hand between the thumb and two fingers with medium pressure. Count the number of strokes until drag/skip is felt in the middle portion of the hair switch consistently for 2 consecutive strokes. This number of strokes is recorded as the Rinse Count Drag. The strokes should be at a rate of 1 stroke per second to a total of 20 strokes (Scale: 1=quick rinse/clean feel to 20=slow rinse/dirty feel).

After the 30 second rinse stroke the hair from top to bottom with non-dominant hand between the thumb and two fingers with medium pressure to remove access water. Repeat stroke of hair switch and assess the clean feel of the hair. This is recorded as the Post Rinse—Clean Feel (Scale: 0=Low/Dirty to 10=High/Clean).

F. Puff Lather Method

First, start water to allow it to reach desired temperature 37.5-38 C. Next, fluff the puff and wet it under the water. Apply the shampoo in a circular motion over top of the puff. Then move puff with lathered product overtop of a beaker. Next squeeze puff in a half turn forward direction 10 times. Repeat with squeeze and half turn in a backward direction 10 times. Lastly, squeeze puff to get all remaining lather out. Measure the amount of lather generated in the beaker.

G. Cylinder Lather Method—Lather Volume

Obtain 100 ml of Water in a 1,000 ml graduated cylinder. Then add 0.5 g of shampoo. The graduated cylinder is on a rotating apparatus. Rotate the cylinder for 25 complete revolutions at a rate of 10 revolutions per 18 seconds to create a lather and stop in a level, vertical position. A timer is set to allow 15 seconds for drainage. After 15 seconds, the lather volume is measured by recording the lather height to the nearest 10 ml mark (including any water that has drained to the bottom on top of which the lather is floating).

H. Kruss Lather Method

KRUSS Dynamic Foam Analyzer is used to evaluate lather. Add shampoo and water into device 1(shampoo):9 (water) dilution. Air going through the chamber generates lather. The speed to lather, lather volume, and bubble size are recorded.

EXAMPLES

The shampoo compositions illustrated in the following Examples illustrate specific embodiments of the shampoo compositions described herein, but are not intended to be limiting thereof. Other modifications can be undertaken by the skilled artisan without departing from the spirit and scope of this invention. These exemplified embodiments of the shampoo composition provide consumer desired mildness, moisture, slip feel, cleaning and viscosity.

The shampoo compositions illustrated in the following Examples are prepared by conventional formulation and mixing methods, an example of which is set forth below. All exemplified amounts are listed as weight percent's and exclude minor materials such as diluents, preservatives, color solutions, imagery ingredients, botanicals, and so forth, unless otherwise specified. All percentages are based on weight unless otherwise specified.

TABLE 1

Examples of Shampoo Compositions

| Phase Stability | Ex. 1 one phase | Ex. 2 one phase | Ex. 3 one phase | Ex. 4 one phase | Ex. 5 one phase | Ex. 6 one phase | Ex. 7 one phase | Ex. 8 one phase |
| --- | --- | --- | --- | --- | --- | --- | --- | --- |
| Viscosity (Pa-s) | 6.137 | 5.970 | 3.826 | 2.533 | 4.405 | 8.683 | 5.823 | 6.394 |
| Decyl Glucoside [1] | 12 | 12 | 12 | 12 | 12 | 12 | 12 | 12 |
| Guar (Excel) [2] | 0.2 | 0.4 | 0.6 | 0.8 | 1 | 0.2 | 0.2 | 0.4 |
| Sclerotium Gum [3] | 0.8 | 0.6 | 0.4 | 0.2 | 0.2 | 1 | | |
| Sclerotium Gum [4] | | | | | | | 0.8 | 0.6 |
| Sodium Benzoate | 0.6 | 0.6 | 0.6 | 0.6 | 0.6 | 0.6 | 0.6 | 0.6 |
| Citric Acid | 0.4 | 0.4 | 0.4 | 0.4 | 0.4 | 0.4 | 0.4 | 0.4 |
| Water | Q. S. | Q. S. | Q. S. | Q. S. | Q. S. | Q. S. | Q. S. | Q. S. |

TABLE 2

| Comparative Examples of Shampoo Compositions | | | | | | |
|---|---|---|---|---|---|---|
| Phase Stability | C1<br>Multiple phases | C2<br>Multiple phases | C3<br>Multiple phases | C4<br>Multiple phases | C5<br>One phase | C6<br>One phase |
| Viscosity (Pa-s) | n/a | n/a | n/a | n/a | 21.115 | 0.541 |
| Decyl Glucoside [1] | 12 | 12 | 12 | 12 | 12 | 12 |
| Guar (Excel) [2] | 0.95 | 0.95 | 0.25 | 0.95 | 1.1 | 0.1 |
| Sodium Benzoate | 0.6 | 0.6 | 0.6 | 0.6 | 0.6 | 0.6 |
| Citric Acid | 0.4 | 0.4 | 0.4 | 0.4 | 0.4 | 0.4 |
| Sclerotium Gum [3] | | | | | 1.1 | 0.1 |
| Xanthan Gum | | | 0.6 | | | |
| Konjac Gum [5] | 0.6 | | | | | |
| Caesalpina Spinosa Gum [6] | | 1.0 | | | | |
| Guar Gum [7] | | | | 1.0 | | |
| Water | Q. S. | Q. S. | Q. S. | Q. S. | Q. S. | Q. S. |

1. PLANTAREN 2000 from BASF
2. JAGUAR EXCEL from Solvay
3. AMIGUM ER from Alban Muller
4. ACTIGUM CS 11 QD from Cargill
5. NUTRICOL XP3464 from FMC
6. SOLAGUM TARA from Seppic
7. SUPERCOL U2 from Ashland As can be seen in the data for the Examples and Comparative Examples, the Comparative Examples C1-C4 contain gums in combination with cationic guar that are not phase stable. Comparative Example C5 is phase stable however it is too viscous. It is consumer desired that a Shampoo is less than 20 Pa-s for ease of spreading in hand. Comparative Example C6 is phase stable however low viscosity. It is consumer desired that a Shampoo is greater than 0.6 Pa-s to avoid running off the hands during use.

It will be appreciated that other modifications of the present disclosure are within the skill of those in the hair care formulation art can be undertaken without departing from the spirit and scope of this invention. All parts, percentages, and ratios herein are by weight unless otherwise specified. Some components may come from suppliers as dilute solutions. The levels given reflect the weight percent of the active material, unless otherwise specified. A level of perfume and/or preservatives may also be included in the following examples.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

What is claimed is:

1. A shampoo composition comprising:
   a) about 5 wt % to about 35 wt % of alkyl polyglucoside;
   b) about 0.15 wt % to about 1.05 wt % sclerotium gum;
   c) about 0.15 wt % to about 1.05 wt % of cationic polymer; and
   d) less than 1% ionic surfactant,
   wherein the shampoo composition has a viscosity of about 0.6 Pa-s to about 20 Pa-s.

2. The shampoo composition of claim 1, comprising about 0.15 wt % to about 1.05 wt % cationic guar.

3. The shampoo composition of claim 2, comprising about 0.2 wt % to about 1.0 wt % cationic guar.

4. The shampoo composition of claim 1, wherein the alkyl polyglucoside is selected from decyl glucoside, caprylyl glucoside, caprylyl/capryl glucoside, undecyl glucoside, octyl glucoside and combinations thereof.

5. The shampoo composition of claim 4, wherein the alkyl polyglucoside comprises decyl glucoside.

6. The shampoo composition of claim 4, comprising about 5 wt % to about 25 wt % of the decyl glucoside.

7. The shampoo composition of claim 4, comprising about 7 wt % to about 20 wt % of the decyl glucoside.

8. The shampoo composition of claim 1, wherein the composition is substantially free of a surfactant selected from sodium alkyl sulfate, sodium cocoyl isethionate, sodium lauroyl sarcosinate, cocamidopropyl betaine, sodium lauroamphoacetate, cetyltrimethylammonium chloride, behenyltrimethylammonium chloride and mixtures thereof.

9. The shampoo composition of claim 1, wherein the non-ionic surfactant is a decyl glucoside having the structure:

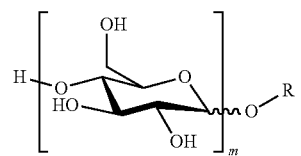

in which R is an alkyl or alkenyl group having about 10 carbons, and m is 1.

10. The shampoo composition of claim 1, wherein the viscosity is about 1.0 Pa-s to about 18 Pa-s.

11. The shampoo composition of claim 1, wherein the viscosity is about 2 Pa-s to about 15 Pa-s.

12. The shampoo composition of claim 1, wherein the composition further comprises a material selected from tea extracts, grape seed extracts, safflower oil, jojoba oil, argon oil, and combinations thereof.

13. The shampoo composition of claim 1, wherein the composition further comprises an anti-microbial agent selected from azoles, climbazole, ketoconazole, itraconazole, econazole, elubiol, hydroxy pyridones, piroctone olamine, ciclopirox, rilopirox, MEA-hydroxyoctyloxypyridinon, kerolytic agents, salicylic acid, hydroxy acids, strobilurins, azoxystrobin, metal chelators, 1,10-phenanthroline, and combinations thereof.

* * * * *